(12) United States Patent
Whitehead et al.

(10) Patent No.: US 6,780,621 B2
(45) Date of Patent: Aug. 24, 2004

(54) **GUAVA (*PSIDIUM GUAJAVA*) 13-HYDROPEROXIDE LYASE AND USES THEREOF**

(75) Inventors: Ian Michael Whitehead, Geneva (CH); Alan John Slusarenko, Hergenrath (BE); Urs Wäspi, Zürich (CH); Duncan James Horatio Gaskin, Reading (GB); Alan Richard Brash, Brentwood, TN (US); Nathalie Tijet, Nashville, TN (US)

(73) Assignees: Firmenich SA, Geneva (CH); Vanderbilt University, Nashville, TN (US); The University of Zurich, Zurich (CH)

( * ) Notice: Subject to any disclaimer, the term of this patent is extended or adjusted under 35 U.S.C. 154(b) by 0 days.

(21) Appl. No.: 10/042,991

(22) Filed: Jan. 9, 2002

(65) Prior Publication Data

US 2002/0142407 A1 Oct. 3, 2002

Related U.S. Application Data

(62) Division of application No. 09/578,533, filed on May 24, 2000.

(51) Int. Cl.[7] .............................. C12P 7/40; C12N 9/88; C12N 1/20
(52) U.S. Cl. ........................... 435/136; 435/183; 435/6; 435/25; 435/232; 435/320.1; 435/252.3; 530/350
(58) Field of Search .......................... 530/350; 435/183, 435/6, 136, 25, 232, 320.1, 252.3

(56) References Cited

U.S. PATENT DOCUMENTS

| | | | |
|---|---|---|---|
| 5,464,761 A | 11/1995 | Muller et al. | ................ 435/147 |
| 6,271,018 B1 | 8/2001 | Brash et al. | ............. 435/252.3 |

FOREIGN PATENT DOCUMENTS

| | | |
|---|---|---|
| EP | 0801133 A2 | 10/1997 |
| WO | WO 00/00627 | 1/2000 |

OTHER PUBLICATIONS

Noordermeer, M. A., Veldink, G. A., Vliegenthart, J. (1999). Alfalfa contains substantial 9–hydroperoxide lyase activity and a 3Z:2E–enal isomerase. FEBS LETT. 443:201–204.

J. Rudinger (1976). Characteristics of the amino acids as components of a peptide hormone sequence. In: Peptide Hormes. Ed . J. A. Parsons. University Park Press, Baltimore, MD pp. 1–7.

Ngo et al. (1994). Computational complexity. protein structure prediction, and the ILevinthal paradox. In: The Protein Folding Problem and Tertiary Structure Prediction. Eds. Merz et al. Birkhauser et al. Boston, MA. pp. 491–495.

Thornton et al. (1995). Protein Engineering: Editiorial Overivew. Current Opinion in Biotechnology 6(4):367–369.

Wallace (1993). Understanding cytochrome c function: engineering protein structure by semisynthesis. The FASEB Journal 7:505–515.

Hornostaj and Robinson (1999), Purification of hydroperoxide lyase from cucumbers. Food Chemistry 66:173–180.

Itoh and Vick (1999). The purification and characterization of fatty acid hydroperoxide lyase in sunflower. Biochim. Biophys. Acta 1436:531–540.

Kim and Gosch (1981). Partial Purification and Properties of a Hydroperoxide Lyase from Fruits of Pear. J. Agri. Food Chem. 29:1220–1225.

Fauconnier, M.L, Perez, A.G., Sanz, C., Marlier, M. (1997). Purification and Characterization of Tomato Leaf (*Lycopersicon esculentum* Mill.) Hydroperoxide Lyase. *J. Agric. Food Chem.* 45:4232.

Matsui K., Shibata Y., Kajiwara, T. and Hatanaka A. (1989). Separation of 13 and 9–hydroperoxide lyase activities in cotyledons of cucumber seedlings. Z. *Naturforsch.* 44c:883–885.

Matsui K, Toyota H., Kajiwara T., Kakuno T. and Hatanaka A. (1991). Fatty acid hydroperoxide cleaving enzyme, hydroperoxide lyase, from tea leaves. *Phytochemistry* 30:2109–2113.

Matsui K., Shibutani M., Hase T., and Kajiwara T. Bell Pepper Fruit Fatty Acid Hydroperoxide Lyase is a Cytochrome P–450 (CYP74B). *FEBS Lett.* 394:21–24 (1996).

Olias J.M., Rios J.J., Valle M., Zamora R., Sanz L.C. and Axelrod B. (1990). Fatty acid hydroperoxide lyase in germinating soybean seedlings. *J. Agric. Food Chem.* 38:624–630.

Schreier P. and Lorenz G. (1982). Separation, partial purification and characterization of a fatty acid hydroperoxide cleaving enzyme from apple and tomato fruits. Z. *Naturforsch.* 37c:165–173.

Shibata Y., Matsui K, Kajiwara T. and Hatanaka, A. (1995). Purification and properties of fatty acid hydroperoxide lyase from green bell pepper fruits. *Plant Cell Physiology* 36:147–156.

Tressl, R. and Drawert, F. (1973). Biogenesis of banana volatiles. *J. Agric. Food Chem.* 21:560–565.

Vick B.A. and Zimmerman D.C. (1976). Lipoxygenase and hydroperoxide lyase in germinating watermelon seedlings. *Plant Physiol.* 57:780–788.

*Primary Examiner*—Richard Hutson
(74) *Attorney, Agent, or Firm*—Needle & Rosenberg, P.C.

(57) ABSTRACT

The present invention relates to fatty acid 13-hydroperoxide lyase protein from guava (*Psidium guajava*) and the gene encoding the protein. Expression systems for recombinant guava 13-hydroperoxide lyase and methods of using recombinant guava 13-hydroperoxide lyase for the production of green notes are provided.

15 Claims, 4 Drawing Sheets

```
Residue No.      301 302 303 304 305 306 307 308 309 310 311 312 313 314 315 316 317 318 319 320 321 322 323 324 325 326 327 328 329 330 331 332 333 334 335 336 337 338 339 340 341 342 343 344 345 346 347 348 349 350
Nucleotide codon ATC CTC GGC TTC AAC GCC TTC GGC GGC TTC TGC AIC CTC CCG ACG TTG CTG AGC AAC ATA CTT AGC GAC ACA ACC GAC GAG CCC CTG CAG CTG GAC CGC AGG ATC CGA AAG GAG GTC CGG GCA AAG GGA CCC GGC TTC ACC TTC GCC TCC GTG AAG
Amino acid        I   L   G   F   N   A   F   G   G   F   S   I   F   L   P   T   I   L   S   N   I   L   S   D   T   T   G   L   Q   D   R   I   R   K   E   V   R   A   K   G   G   P   A   L   S   F   A   S   V   K Residue No.      351 352 353 354 355 356 357 358 359 360 361 362 363 364 365 366 367 368 369 370 371 372 373 374 375 376 377 378 379 380 381 382 383 384 385 386 387 388 389 390 391 392 393 394 395 396 397 398 399 400
Nucleotide codon GAG ATG GAA CTC GTG AAG TCG CAC GTC GAG CTC CGG CTC AAC CCG CCC GTC AAC CCC CCC TTC CAA TAC GCT CGA GCC CGG AAG GAC GAC TTC CAG CTC AAG TGC CAC CAC GAC TCT GTC TTT GAT GTC AAG AAA GGC GAG CTG CTA TGC
Amino acid        E   M   E   L   V   K   S   H   V   Y   Y   E   T   L   R   L   N   P   P   V   P   F   Q   Y   A   R   A   R   K   D   F   Q   L   K   S   H   H   D   S   Y   F   D   V   K   K   G   E   L   L   C Residue No.      401 402 403 404 405 406 407 408 409 410 411 412 413 414 415 416 417 418 419 420 421 422 423 424 425 426 427 428 429 430 431 432 433 434 435 436 437 438 439 440 441 442 443 444 445 446 447 448 449 450
Nucleotide codon CAG AAG GTC GTG ATC ACA GAC CCG AAA GTG TTC GAC GAA CCG GAG CCG AGC TTC AAC TCC GAC CGC TTC GTC CAG AAC AGC GAG CTA CTG GAT TAC CTC TAC CTG TCC AAC GGC CCC CAG CCG ACC ATC GAA ACC TGC AAC GGC TGC
Amino acid        Q   K   V   V   I   T   D   P   K   V   F   D   E   P   E   P   S   F   N   S   D   R   F   V   Q   N   S   E   L   L   D   Y   L   Y   L   S   N   G   P   Q   P   T   I   E   S   N   K   Q   C Residue No.      451 452 453 454 455 456 457 458 459 460 461 462 463 464 465 466 467 468 469 470 471 472 473 474 475 476 477 478 479 480 481 482 483 484 485 486 487 488
Nucleotide codon GCC GCT AAG GAC TAC GTC ATC CTC ATC GCC TGT CTC TTC GTT GCC TAC ATG TTT CGA CGG TAC AGG AGC GTT ACA GGA AGC AGC AGC ATC ACA GCA GTT GAA AAG GCC AAC         SEQ ID NO:27
Amino acid        A   A   K   D   Y   V   I   L   I   A   C   L   F   V   A   Y   M   F   R   R   Y   R   S   V   T   G   S   S   S   I   T   A   V   E   K   A   N              SEQ ID NO:6
```

Heme Binding Site

SEQUENCE LISTING

<160> NUMBER OF SEQ ID NOS: 27

<210> SEQ ID NO 1
<211> LENGTH: 7
<212> TYPE: PRT
<213> ORGANISM: Psidium Guajava (guava)

<400> SEQUENCE: 1

Thr Tyr Pro Pro Ser Leu Ser
 1               5

<210> SEQ ID NO 2
<211> LENGTH: 476
<212> TYPE: PRT
<213> ORGANISM: Psidium Guajava (guava)

<400> SEQUENCE: 2

Met Ser Ser Thr Tyr Pro Pro Ser Leu Ser Pro Ser Pro Arg
 1               5                  10                  15

Pro Thr Thr Leu Pro Val Arg Thr Ile Pro Gly Ser Tyr Gly Trp Pro
                20                  25                  30

Leu Leu Gly Pro Ile Ser Asp Arg Leu Asp Tyr Phe Trp Phe Gln Gly
            35                  40                  45

Pro Glu Thr Phe Phe Arg Lys Arg Ile Glu Lys Tyr Lys Ser Thr Val
    50                  55                  60

Phe Arg Ala Asn Val Pro Pro Cys Phe Pro Phe Phe Ser Asn Val Asn
65                  70                  75                  80

Pro Asn Val Val Val Leu Asp Cys Glu Ser Phe Ala His Leu Phe
                85                  90                  95

Asp Met Glu Ile Val Glu Lys Ser Asn Val Leu Val Gly Asp Phe Met
                100                 105                 110

Pro Ser Val Lys Tyr Thr Gly Asn Ile Arg Val Cys Ala Tyr Leu Asp
            115                 120                 125

Thr Ser Glu Pro Gln His Ala Gln Val Lys Asn Phe Ala Met Asp Ile
    130                 135                 140

Leu Lys Arg Ser Ser Lys Val Trp Glu Ser Glu Val Ile Ser Asn Leu
145                 150                 155                 160

Asp Thr Met Trp Asp Thr Ile Glu Ser Ser Leu Ala Lys Asp Gly Asn
                165                 170                 175

Ala Ser Val Ile Phe Pro Leu Gln Lys Phe Leu Phe Asn Phe Leu Ser
            180                 185                 190

Lys Ser Ile Ile Gly Ala Asp Pro Ala Ala Ser Pro Gln Val Ala Lys
        195                 200                 205

Ser Gly Tyr Ala Met Leu Asp Arg Trp Leu Ala Leu Gln Leu Leu Pro
    210                 215                 220

Thr Ile Asn Ile Gly Val Leu Gln Pro Leu Val Glu Ile Phe Leu His
225                 230                 235                 240

Ser Trp Ala Tyr Pro Phe Ala Leu Val Ser Gly Asp Tyr Asn Lys Leu
                245                 250                 255

Tyr Gln Phe Ile Glu Lys Glu Gly Arg Glu Ala Val Glu Arg Ala Lys
            260                 265                 270

Ala Glu Phe Gly Leu Thr His Gln Glu Ala Ile His Asn Leu Leu Phe
        275                 280                 285

Ile Leu Gly Phe Asn Ala Phe Gly Gly Phe Ser Ile Phe Leu Pro Thr
    290                 295                 300

```
Leu Leu Ser Asn Ile Leu Ser Asp Thr Thr Gly Leu Gln Asp Arg Leu
305                 310                 315                 320

Arg Lys Glu Val Arg Ala Lys Gly Gly Pro Ala Leu Ser Phe Ala Ser
                325                 330                 335

Val Lys Glu Met Glu Leu Val Lys Ser Val Val Tyr Glu Thr Leu Arg
                340                 345                 350

Leu Asn Pro Pro Val Pro Phe Gln Tyr Ala Arg Ala Arg Lys Asp Phe
                355                 360                 365

Gln Leu Lys Ser His Asp Ser Val Phe Asp Val Lys Lys Gly Glu Leu
                370                 375                 380

Leu Cys Gly Tyr Gln Lys Val Val Met Thr Asp Pro Lys Val Phe Asp
385                 390                 395                 400

Glu Pro Glu Ser Phe Asn Ser Asp Arg Phe Val Gln Asn Ser Glu Leu
                405                 410                 415

Leu Asp Tyr Leu Tyr Trp Ser Asn Gly Pro Gln Thr Gly Thr Pro Thr
                420                 425                 430

Glu Ser Asn Lys Gln Cys Ala Ala Lys Asp Tyr Val Thr Leu Thr Ala
                435                 440                 445

Cys Leu Phe Val Ala Tyr Met Phe Arg Arg Tyr Asn Ser Val Thr Gly
450                 455                 460

Ser Ser Ser Ser Ile Thr Ala Val Glu Lys Ala Asn
465                 470                 475

<210> SEQ ID NO 3
<211> LENGTH: 480
<212> TYPE: PRT
<213> ORGANISM: Psidium Guajava (guava)

<400> SEQUENCE: 3

Met Ser Pro Ala Met Ser Ser Thr Tyr Pro Ser Leu Ser Pro Pro
  1               5                  10                  15

Ser Ser Pro Arg Pro Thr Thr Leu Pro Val Arg Thr Ile Pro Gly Ser
                 20                  25                  30

Tyr Gly Trp Pro Leu Leu Gly Pro Ile Ser Asp Arg Leu Asp Tyr Phe
                 35                  40                  45

Trp Phe Gln Gly Pro Glu Thr Phe Phe Arg Lys Arg Ile Glu Lys Tyr
      50                   55                  60

Lys Ser Thr Val Phe Arg Ala Asn Val Pro Pro Cys Phe Pro Phe Phe
 65                   70                  75                  80

Ser Asn Val Asn Pro Asn Val Val Val Leu Asp Cys Glu Ser Phe
                 85                  90                  95

Ala His Leu Phe Asp Met Glu Ile Val Glu Lys Ser Asn Val Leu Val
                100                 105                 110

Gly Asp Phe Met Pro Ser Val Lys Tyr Thr Gly Asn Ile Arg Val Cys
                115                 120                 125

Ala Tyr Leu Asp Thr Ser Glu Pro Gln His Ala Gln Val Lys Asn Phe
                130                 135                 140

Ala Met Asp Ile Leu Lys Arg Ser Ser Lys Val Trp Glu Ser Glu Val
145                 150                 155                 160

Ile Ser Asn Leu Asp Thr Met Trp Asp Thr Ile Glu Ser Ser Leu Ala
                165                 170                 175

Lys Asp Gly Asn Ala Ser Val Ile Phe Pro Leu Gln Lys Phe Leu Phe
                180                 185                 190
```

-continued

```
Asn Phe Leu Ser Lys Ser Ile Ile Gly Ala Asp Pro Ala Ala Ser Pro
            195                 200                 205

Gln Val Ala Lys Ser Gly Tyr Ala Met Leu Asp Arg Trp Leu Ala Leu
    210                 215                 220

Gln Leu Leu Pro Thr Ile Asn Ile Gly Val Leu Gln Pro Leu Val Glu
225                 230                 235                 240

Ile Phe Leu His Ser Trp Ala Tyr Pro Phe Ala Leu Val Ser Gly Asp
                245                 250                 255

Tyr Asn Lys Leu Tyr Gln Phe Ile Glu Lys Glu Gly Arg Glu Ala Val
            260                 265                 270

Glu Arg Ala Lys Ala Glu Phe Gly Leu Thr His Gln Glu Ala Ile His
        275                 280                 285

Asn Leu Leu Phe Ile Leu Gly Phe Asn Ala Phe Gly Gly Phe Ser Ile
    290                 295                 300

Phe Leu Pro Thr Leu Leu Ser Asn Ile Leu Ser Asp Thr Thr Gly Leu
305                 310                 315                 320

Gln Asp Arg Leu Arg Lys Glu Val Arg Ala Lys Gly Gly Pro Ala Leu
                325                 330                 335

Ser Phe Ala Ser Val Lys Glu Met Glu Leu Val Lys Ser Val Val Tyr
            340                 345                 350

Glu Thr Leu Arg Leu Asn Pro Pro Val Pro Phe Gln Tyr Ala Arg Ala
        355                 360                 365

Arg Lys Asp Phe Gln Leu Lys Ser His Asp Ser Val Phe Asp Val Lys
    370                 375                 380

Lys Gly Glu Leu Leu Cys Gly Tyr Gln Lys Val Val Met Thr Asp Pro
385                 390                 395                 400

Lys Val Phe Asp Glu Pro Glu Ser Phe Asn Ser Asp Arg Phe Val Gln
                405                 410                 415

Asn Ser Glu Leu Leu Asp Tyr Leu Tyr Trp Ser Asn Gly Pro Gln Thr
            420                 425                 430

Gly Thr Pro Thr Glu Ser Asn Lys Gln Cys Ala Ala Lys Asp Tyr Val
        435                 440                 445

Thr Leu Thr Ala Cys Leu Phe Val Ala Tyr Met Phe Arg Arg Tyr Asn
    450                 455                 460

Ser Val Thr Gly Ser Ser Ser Ile Thr Ala Val Glu Lys Ala Asn
465                 470                 475                 480

<210> SEQ ID NO 4
<211> LENGTH: 483
<212> TYPE: PRT
<213> ORGANISM: Psidium Guajava (guava)

<400> SEQUENCE: 4

Met Ser Asn Met Ser Pro Ala Met Ser Ser Thr Tyr Pro Pro Ser Leu
1               5                   10                  15

Ser Pro Pro Ser Ser Pro Arg Pro Thr Thr Leu Pro Val Arg Thr Ile
            20                  25                  30

Pro Gly Ser Tyr Gly Trp Pro Leu Leu Gly Pro Ile Ser Asp Arg Leu
        35                  40                  45

Asp Tyr Phe Trp Phe Gln Gly Pro Glu Thr Phe Arg Lys Arg Ile
    50                  55                  60

Glu Lys Tyr Lys Ser Thr Val Phe Arg Ala Asn Val Pro Pro Cys Phe
65                  70                  75                  80

Pro Phe Phe Ser Asn Val Asn Pro Asn Val Val Val Leu Asp Cys
```

```
                85                  90                  95
Glu Ser Phe Ala His Leu Phe Asp Met Glu Ile Val Glu Lys Ser Asn
            100                 105                 110
Val Leu Val Gly Asp Phe Met Pro Ser Val Lys Tyr Thr Gly Asn Ile
            115                 120                 125
Arg Val Cys Ala Tyr Leu Asp Thr Ser Glu Pro Gln His Ala Gln Val
            130                 135                 140
Lys Asn Phe Ala Met Asp Ile Leu Lys Arg Ser Ser Lys Val Trp Glu
145                 150                 155                 160
Ser Glu Val Ile Ser Asn Leu Asp Thr Met Trp Asp Thr Ile Glu Ser
                165                 170                 175
Ser Leu Ala Lys Asp Gly Asn Ala Ser Val Ile Phe Pro Leu Gln Lys
            180                 185                 190
Phe Leu Phe Asn Phe Leu Ser Lys Ser Ile Ile Gly Ala Asp Pro Ala
            195                 200                 205
Ala Ser Pro Gln Val Ala Lys Ser Gly Tyr Ala Met Leu Asp Arg Trp
            210                 215                 220
Leu Ala Leu Gln Leu Leu Pro Thr Ile Asn Ile Gly Val Leu Gln Pro
225                 230                 235                 240
Leu Val Glu Ile Phe Leu His Ser Trp Ala Tyr Pro Phe Ala Leu Val
                245                 250                 255
Ser Gly Asp Tyr Asn Lys Leu Tyr Gln Phe Ile Glu Lys Glu Gly Arg
            260                 265                 270
Glu Ala Val Glu Arg Ala Lys Ala Glu Phe Gly Leu Thr His Gln Glu
            275                 280                 285
Ala Ile His Asn Leu Leu Phe Ile Leu Gly Phe Asn Ala Phe Gly Gly
            290                 295                 300
Phe Ser Ile Phe Leu Pro Thr Leu Leu Ser Asn Ile Leu Ser Asp Thr
305                 310                 315                 320
Thr Gly Leu Gln Asp Arg Leu Arg Lys Glu Val Arg Ala Lys Gly Gly
                325                 330                 335
Pro Ala Leu Ser Phe Ala Ser Val Lys Glu Met Glu Leu Val Lys Ser
            340                 345                 350
Val Val Tyr Glu Thr Leu Arg Leu Asn Pro Pro Val Pro Phe Gln Tyr
            355                 360                 365
Ala Arg Ala Arg Lys Asp Phe Gln Leu Lys Ser His Asp Ser Val Phe
            370                 375                 380
Asp Val Lys Lys Gly Glu Leu Leu Cys Gly Tyr Gln Lys Val Val Met
385                 390                 395                 400
Thr Asp Pro Lys Val Phe Asp Glu Pro Glu Ser Phe Asn Ser Asp Arg
                405                 410                 415
Phe Val Gln Asn Ser Glu Leu Leu Asp Tyr Leu Tyr Trp Ser Asn Gly
            420                 425                 430
Pro Gln Thr Gly Thr Pro Thr Glu Ser Asn Lys Gln Cys Ala Ala Lys
            435                 440                 445
Asp Tyr Val Thr Leu Thr Ala Cys Leu Phe Val Ala Tyr Met Phe Arg
            450                 455                 460
Arg Tyr Asn Ser Val Thr Gly Ser Ser Ser Ile Thr Ala Val Glu
465                 470                 475                 480
Lys Ala Asn

<210> SEQ ID NO 5
<211> LENGTH: 8
```

<212> TYPE: PRT
<213> ORGANISM: Psidium Guajava (guava)

<400> SEQUENCE: 5

```
Met Ala Arg Val Val Met Ser Asn
  1               5
```

<210> SEQ ID NO 6
<211> LENGTH: 488
<212> TYPE: PRT
<213> ORGANISM: Psidium Guajava (guava)

<400> SEQUENCE: 6

```
Met Ala Arg Val Val Met Ser Asn Met Ser Pro Ala Met Ser Ser Thr
  1               5                  10                  15

Tyr Pro Pro Ser Leu Ser Pro Ser Ser Pro Arg Pro Thr Thr Leu
                 20                  25                  30

Pro Val Arg Thr Ile Pro Gly Ser Tyr Gly Trp Pro Leu Leu Gly Pro
             35                  40                  45

Ile Ser Asp Arg Leu Asp Tyr Phe Trp Phe Gln Gly Pro Glu Thr Phe
 50                  55                  60

Phe Arg Lys Arg Ile Glu Lys Tyr Lys Ser Thr Val Phe Arg Ala Asn
 65                  70                  75                  80

Val Pro Pro Cys Phe Pro Phe Ser Asn Val Asn Pro Asn Val Val
                 85                  90                  95

Val Val Leu Asp Cys Glu Ser Phe Ala His Leu Phe Asp Met Glu Ile
                100                 105                 110

Val Glu Lys Ser Asn Val Leu Val Gly Asp Phe Met Pro Ser Val Lys
            115                 120                 125

Tyr Thr Gly Asn Ile Arg Val Cys Ala Tyr Leu Asp Thr Ser Glu Pro
130                 135                 140

Gln His Ala Gln Val Lys Asn Phe Ala Met Asp Ile Leu Lys Arg Ser
145                 150                 155                 160

Ser Lys Val Trp Glu Ser Glu Val Ile Ser Asn Leu Asp Thr Met Trp
                165                 170                 175

Asp Thr Ile Glu Ser Ser Leu Ala Lys Asp Gly Asn Ala Ser Val Ile
            180                 185                 190

Phe Pro Leu Gln Lys Phe Leu Phe Asn Phe Leu Ser Lys Ser Ile Ile
        195                 200                 205

Gly Ala Asp Pro Ala Ala Ser Pro Gln Val Ala Lys Ser Gly Tyr Ala
    210                 215                 220

Met Leu Asp Arg Trp Leu Ala Leu Gln Leu Leu Pro Thr Ile Asn Ile
225                 230                 235                 240

Gly Val Leu Gln Pro Leu Val Glu Ile Phe Leu His Ser Trp Ala Tyr
                245                 250                 255

Pro Phe Ala Leu Val Ser Gly Asp Tyr Asn Lys Leu Tyr Gln Phe Ile
            260                 265                 270

Glu Lys Glu Gly Arg Glu Ala Val Glu Arg Ala Lys Ala Glu Phe Gly
        275                 280                 285

Leu Thr His Gln Glu Ala Ile His Asn Leu Leu Phe Ile Leu Gly Phe
    290                 295                 300

Asn Ala Phe Gly Gly Phe Ser Ile Phe Leu Pro Thr Leu Leu Ser Asn
305                 310                 315                 320

Ile Leu Ser Asp Thr Thr Gly Leu Gln Asp Arg Leu Arg Lys Glu Val
                325                 330                 335
```

```
Arg Ala Lys Gly Gly Pro Ala Leu Ser Phe Ala Ser Val Lys Glu Met
            340                 345                 350

Glu Leu Val Lys Ser Val Val Tyr Glu Thr Leu Arg Leu Asn Pro Pro
        355                 360                 365

Val Pro Phe Gln Tyr Ala Arg Ala Arg Lys Asp Phe Gln Leu Lys Ser
    370                 375                 380

His Asp Ser Val Phe Asp Val Lys Lys Gly Glu Leu Leu Cys Gly Tyr
385                 390                 395                 400

Gln Lys Val Val Met Thr Asp Pro Lys Val Phe Asp Glu Pro Glu Ser
                405                 410                 415

Phe Asn Ser Asp Arg Phe Val Gln Asn Ser Glu Leu Leu Asp Tyr Leu
                420                 425                 430

Tyr Trp Ser Asn Gly Pro Gln Thr Gly Thr Pro Thr Glu Ser Asn Lys
            435                 440                 445

Gln Cys Ala Ala Lys Asp Tyr Val Thr Leu Thr Ala Cys Leu Phe Val
    450                 455                 460

Ala Tyr Met Phe Arg Arg Tyr Asn Ser Val Thr Gly Ser Ser Ser Ser
465                 470                 475                 480

Ile Thr Ala Val Glu Lys Ala Asn
                485
```

<210> SEQ ID NO 7
<211> LENGTH: 1431
<212> TYPE: DNA
<213> ORGANISM: Psdium Guajava (guava)

<400> SEQUENCE: 7

```
atgtcgtcca cctaccccc  gtctctgtcc ccgccgtcgt cgccgcggcc gaccaccctc    60
ccggtgcgga cgatcccggg cagctacggg tggcccctcc tcggcccgat atcggaccgc   120
ctggactact tctggttcca aggcccggag acgttcttca ggaagaggat cgagaagtac   180
aagagcaccg tgttccgcgc gaacgtgcct ccgtgcttcc ccttcttctc gaacgtgaac   240
cctaacgtcg tggtcgtcct cgattgcgag tccttcgctc acttgttcga catggagatc   300
gtggagaaga gcaacgtcct cgtcggcgac ttcatgccga gcgtgaagta caccgggaac   360
atccgggtct gcgcttacct cgacacttcc gagcctcaac acgctcaggt gaagaacttt   420
gcgatggaca tactgaagag gagctccaaa gtgtgggaga gcgaagtgat ctcgaacttg   480
gacaccatgt gggacaccat cgagtccagc ctcgccaagg acggcaacgc cagcgtcatc   540
ttccctctcc aaaagttcct cttcaacttc ctctccaagt ccatcatcgg cgctgacccg   600
gccgcctcgc cgcaggtggc caagtccggc tacgccatgc ttgaccggtg gctcgctctc   660
cagctcctcc ccaccatcaa cattggcgta ctgcagcctc tagtggagat ttttctgcat   720
tcttgggcat accctttgc  gctggtgagc ggggactaca acaagctcta ccagttcatc   780
gagaaggaag gccgagaagc ggtcgaaagg gcgaaggccg agttcggatt gacacaccag   840
gaggccatcc acaacttgct gttcatcctc ggcttcaacg cgttcggcgg cttctcgatc   900
ttcctcccca cgttgctgag caacatactt agcgacacaa ccggactgca ggaccggctg   960
aggaaggagg tccgggcaaa gggagggccg gcgttgagct tcgcctcggt gaaggagatg  1020
gaactcgtga agtcggtcgt gtacgagacg ctgcggctca accgcccgt  cccgttccaa  1080
tacgctcgag cccggaagga cttccagctc aagtcccacg actctgtctt tgatgtcaag  1140
aaaggcgagc tgctatgcgg gtatcagaag gtggtgatga cagacccgaa agtgttcgac  1200
```

```
gaaccggaga gcttcaactc ggaccggttc gtccaaaaca gcgagctact ggattacctg    1260
tactggtcca acgggccgca gaccggaacg ccgaccgagt cgaacaagca gtgcgcggct    1320
aaggactacg tcaccctcac cgcttgtctc ttcgttgcct acatgtttcg acggtacaat    1380
tccgtcacag gaagctcgag ctcgatcaca gccgttgaaa aggccaactg a             1431

<210> SEQ ID NO 8
<211> LENGTH: 1443
<212> TYPE: DNA
<213> ORGANISM: Psidium Guajava (guava)

<400> SEQUENCE: 8
atgtcgccgg ccatgtcgtc cacctacccc ccgtctctgt cccgccgtc gtcgccgcgg      60 ccgaccaccc tcccggtgcg gacgatcccg ggcagctacg ggtggcccct cctcggcccg    120
atatcggacc gcctggacta cttctggttc caaggcccgg agacgttctt caggaagagg    180
atcgagaagt acaagagcac cgtgttccgc gcgaacgtgc ctccgtgctt ccccttcttc    240
tcgaacgtga accctaacgt cgtggtcgtc ctcgattgcg agtccttcgc tcacttgttc    300
gacatggaga tcgtggagaa gagcaacgtc tcgtcggcg acttcatgcc gagcgtgaag     360
tacaccggga acatccgggt ctgcgcttac ctcgacactt ccgagcctca acacgctcag    420
gtgaagaact ttgcgatgga catactgaag aggagctcca agtgtgggga gagcgaagtg    480
atctcgaact tggacaccat gtgggacacc atcgagtcca gcctcgccaa ggacggcaac    540
gccagcgtca tcttccctct ccaaaagttc ctcttcaact tcctctccaa gtccatcatc    600
ggcgctgacc cggccgcctc gccgcaggtg gccaagtccg gctacgccat gcttgaccgg    660
tggctcgctc tccagctcct ccccaccatc aacattggcg tactgcagcc tctagtggag    720
atttttctgc attcttgggc atacctttt gcgctggtga gcggggacta caacaagctc    780
taccagttca tcgagaagga aggccgagaa gcggtcgaaa gggcgaaggc cgagttcgga    840
ttgacacacc aggaggccat ccacaacttg ctgttcatcc tcggcttcaa cgcgttcggc    900
ggcttctcga tcttcctccc cacgttgctg agcaacatac ttagcgacac aaccggactg    960
caggaccggc tgaggaagga ggtccgggca aagggagggc cggcgttgag cttcgcctcg   1020
gtgaaggaga tggaactcgt gaagtcggtc gtgtacgaga cgctgcggct caaccccgccc   1080 gtcccgttcc aatacgctcg agcccggaag gacttccagc tcaagtccca cgactctgtc   1140
tttgatgtca agaaggcga gctgctatgc gggtatcaga aggtggtgat gacagacccg    1200
aaagtgttcg acgaaccgga gagcttcaac tcggaccggt tcgtccaaaa cagcgagcta   1260
ctggattacc tgtactggtc caacgggccg cagaccggaa cgccgaccga gtcgaacaag   1320
cagtgcgcgg ctaaggacta cgtcaccctc accgcttgtc tcttcgttgc ctacatgttt   1380
cgacggtaca attccgtcac aggaagctcg agctcgatca cagccgttga aaaggccaac   1440
tga                                                                  1443

<210> SEQ ID NO 9
<211> LENGTH: 1452
<212> TYPE: DNA
<213> ORGANISM: Psidium Guajava (guava)

<400> SEQUENCE: 9
atgagcaaca tgtcgccggc catgtcgtcc acctaccccc cgtctctgtc cccgccgtcg     60
tcgccgcggc cgaccaccct cccggtgcgg acgatcccgg gcagctacgg gtggcccctc    120
ctcggcccga tatcggaccg cctggactac ttctggttcc aaggcccgga gacgttcttc    180
```

```
aggaagagga tcgagaagta caagagcacc gtgttccgcg cgaacgtgcc tccgtgcttc      240
cccttcttct cgaacgtgaa ccctaacgtc gtggtcgtcc tcgattgcga gtccttcgct      300
cacttgttcg acatggagat cgtggagaag agcaacgtcc tcgtcggcga cttcatgccg      360
agcgtgaagt acaccgggaa catccgggtc tgcgcttacc tcgacacttc cgagcctcaa      420
cacgctcagg tgaagaactt tgcgatggac atactgaaga ggagctccaa agtgtgggag      480
agcgaagtga tctcgaactt ggacaccatg tgggacacca tcgagtccag cctcgccaag      540
gacggcaacg ccagcgtcat cttccctctc caaaagttcc tcttcaactt cctctccaag      600
tccatcatcg gcgctgaccc ggccgcctcg ccgcaggtgg ccaagtccgg ctacgccatg      660
cttgaccggt ggctcgctct ccagctcctc cccaccatca acattggcgt actgcagcct      720
ctagtggaga tttttctgca ttcttgggca tacccttttg cgctggtgag cggggactac      780
aacaagctct accagttcat cgagaaggaa ggccgagaag cggtcgaaag ggcgaaggcc      840
gagttcggat tgacacacca ggaggccatc acaacttgc tgttcatcct cggcttcaac      900
gcgttcggcg gcttctcgat cttcctcccc acgttgctga gcaacatact tagcgacaca      960
accggactgc aggaccggct gaggaaggag gtccgggcaa agggagggcc ggcgttgagc     1020
ttcgcctcgg tgaaggagat ggaactcgtg aagtcggtcg tgtacgagac gctgcggctc     1080
aacccgcccg tcccgttcca atacgctcga gcccggaagg acttccagct caagtcccac     1140
gactctgtct ttgatgtcaa gaaggcgag ctgctatgcg ggtatcagaa ggtggtgatg     1200
acagacccga agtgttcga cgaaccggag agcttcaact cggaccggtt cgtccaaaac     1260
agcgagctac tggattacct gtactggtcc aacgggccgc agaccggaac gccgaccgag     1320
tcgaacaagc agtgcgcggc taaggactac gtcaccctca ccgcttgtct cttcgttgcc     1380
tacatgtttc gacggtacaa ttccgtcaca ggaagctcga gctcgatcac agccgttgaa     1440
aaggccaact ga                                                         1452

<210> SEQ ID NO 10
<211> LENGTH: 1467
<212> TYPE: DNA
<213> ORGANISM: Psidium Guajava (guava)

<400> SEQUENCE: 10
atggcgaggg tcgtgatgag caacatgtcg ccggccatgt cgtccaccta cccccgtct       60 ctgtccccgc cgtcgtcgcc gcggccgacc accctcccgg tgcggacgat cccgggcagc      120
tacgggtggc ccctcctcgg cccgatatcg gaccgcctgg actacttctg gttccaaggc      180
ccggagacgt tcttcaggaa gaggatcgag aagtacaaga gcaccgtgtt ccgcgcgaac      240
gtgcctccgt gcttcccctt cttctcgaac gtgaaccta acgtcgtggt cgtcctcgat      300
tgcgagtcct tcgctcactt gttcgacatg gagatcgtgg agaagagcaa cgtcctcgtc      360
ggcgacttca tgccgagcgt gaagtacacc gggaacatcc gggtctgcgc ttacctcgac      420
acttccgagc ctcaacacgc tcaggtgaag aactttgcga tggacatact gaagaggagc      480
tccaaagtgt gggagagcga agtgatctcg aacttggaca ccatgtggga caccatcgag      540
tccagcctcg ccaaggacgg caacgccagc gtcatcttcc ctctccaaaa gttcctcttc      600
aacttcctct ccaagtccat catcggcgct gacccggccg cctcgccgca ggtggccaag      660
tccggctacg ccatgcttga ccggtggctc gctctccagc tcctccccac catcaacatt      720
ggcgtactgc agcctctagt ggagattttt ctgcattctt gggcataccc ttttgcgctg      780
```

```
gtgagcgggg actacaacaa gctctaccag ttcatcgaga aggaaggccg agaagcggtc    840
gaaagggcga aggccgagtt cggattgaca caccaggagg ccatccacaa cttgctgttc    900
atcctcggct tcaacgcgtt cggcggcttc tcgatcttcc tccccacgtt gctgagcaac    960
atacttagcg acacaaccgg actgcaggac cggctgagga aggaggtccg ggcaaaggga   1020
gggccggcgt tgagcttcgc ctcggtgaag gagatggaac tcgtgaagtc ggtcgtgtac   1080
gagacgctgc ggctcaaccc gcccgtcccg ttccaatacg ctcgagcccg gaaggacttc   1140
cagctcaagt cccacgactc tgtctttgat gtcaagaaag gcgagctgct atgcgggtat   1200
cagaaggtgg tgatgacaga cccgaaagtg ttcgacgaac cggagagctt caactcggac   1260
cggttcgtcc aaaacagcga gctactggat tacctgtact ggtccaacgg ccgcagacc    1320 ggaacgccga ccgagtcgaa caagcagtgc gcggctaagg actacgtcac cctcaccgct   1380
tgtctcttcg ttgcctacat gtttcgacgg tacaattccg tcacaggaag ctcgagctcg   1440
atcacagccg ttgaaaaggc caactga                                       1467

<210> SEQ ID NO 11
<211> LENGTH: 1443
<212> TYPE: DNA
<213> ORGANISM: Capsicum annum (green pepper)

<400> SEQUENCE: 11
atgataccta taatgagctc tgctcctcta tcaactgcta caccaatatc tctcccgta    60 cgtaaaattc cagggagcta cgggtttcca ttattagggc cactttggga tcgattagac    120
tataactggt tccaaaagct cccagatttc ttcagcaaga gagtcgaaaa gtataacagc    180
acggtattca gaacgaatgt accgccttgt tttccatttt ttttgggtgt aaatccaaat    240
gtagtggcgg tactggatgt caagtcattt gcacatctat ttgatatgga gattgttgag    300
aaagctaatg tgcttgttgg tgatttcatg cccagtgttg tttatactgg tgatatgcgt    360
gtttgtgctt atcttgatac ttctgaaacct aaacatactc agattaagaa cttttcattg    420
gacatcctaa aaagaagttc aaagacatgg gtgcctacac tagttaaaga acttgataca    480
ctgttcggaa cttttgaatc agatctttca aaatccaaat cagcttctct tctccctgca    540
ttgcaaaaat tcctcttcaa cttcttctcc ttaactttcc tcggggccga tccatcagcc    600
tcaccggaga tagccaactc tggcttcgcc tatcttgatg catggctagc tattcaacta    660
gcacctactg ttagcattgg tgttcttcaa ccccttgaag aaatcttcgt ccactctttt    720
tcatacccct attttcttgt ccgtggaggt tacgaaaaac tcattaagtt tgtgaaaagt    780
gaagctaagg aagtgttaac gagggcacaa acagactttc agctaactga acaagaagcc    840
attcataacc ttttgttcat tcttggattc aatgcttttg gtggtttcac cattttcttg    900
ccaacccttc tgggaaacct tgggagacga gaaaaatgct gagatgcaag agaaactgag    960 aaagaagtg agggaaaaag ttggacaaat caagaaaact tgagttttga gagtgtaaaa   1020
gaaatggaac tggttcagtc ttttgtttat gaatcactta ggctaagccc accagtgcca   1080
agtcaatatg caagagcaag aaaagacttc atgctcagtt cacatgattc agtttacgaa   1140
atcaagaaag gtgaacttct tgtggttac cagccattag tgatgaaaga tccaaaggtg   1200
tttgatgaac ctgaaaagtt tatgttggag aggtttacaa aggagaaagg gaagaattg   1260 ctgaattatt tgttttggtc taatggccca cagactggga gccctactga atcaaacaag   1320
caatgtgctg ctaaggatgc ggttactctt actgcttctt tgattgtggc ttacattttc   1380
caaaagtatg attctgtgag tttctcatct ggttcactca catctgtgaa aaaagcctgc   1440
```

```
                                                     -continued tga                                                                    1443

<210> SEQ ID NO 12
<211> LENGTH: 1638
<212> TYPE: DNA
<213> ORGANISM: Musa sp. (banana)

<400> SEQUENCE: 12
aagaagaaga gagggaaggt acggatggct atgatgtggt cgtcagcctc cgccaccgcc        60
gtcaccacgc tgccgacgag gcccatccct ggaagctacg gcccgccgct ggtgggcccc       120
ctcaaggacc gcctcgacta cttctggttt cagggaccgg agaccttctt ccgcagccgg       180
atggccaccc acaagagcac cgtgttccgc accaacatgc cccccacctt ccccttcttc       240
gttggagtcg accccgcgt ggtcaccgtc ctcgactgca catccttctc cgccctcttc        300
gacctcgagg tcgtggagaa gaagaacatt ctcatcgggg actacatgcc cagcctcagc       360
ttcaccggcg acacccgcgt cgtcgtgtac ctcgaccct ccgagcccga ccacgcccgc        420
gtgaagagct ctgcttgga actcctcagg cgcggcgcca agacctgggt ctcctcgttc        480
ctctccaatc tcgatgtcat gctcgccacc atagagcagg ggatcgccaa ggatggctcc       540
gccggcttat tcggcccgct gcagaagtgc atcttcgcgt tcctctgcaa gagcatcatc       600
ggggccgacc cgtcggtgtc gcccgacgtg ggagaaaatg gcttcgtcat gctcgacaag       660
tggcttgcgc tgcagctcct cccgacggtg aaggtcgggg ccatcccgca accctggag       720 gagatcctcc tccactcctt cccctccc ttcttcctcg tgagccgcga ttaccggaag         780
ctgtacgaat tcgtcgagaa gcaaggccaa gaggttgtcc ggcgagcgga aaccgagcac       840
gggctcagca agcacgacgc catcaacaac atcttgttcg tcctaggatt caacgccttc       900
ggcggcttct cggtcttctt ccccacgctc ctgaccacca tagggaggga caagacgggc       960
ctgcgggaga agctcaagga cgaggtgcgc agggtcatga gagtagagg ggagaagcgg       1020 ccgagcttcg agacggtgcg ggagatggag ctggtgcgat cgacggtgta cgaggtcctg      1080
cggctgaacc gccggtgcc gctgcagtac gggcgggcgc gcaccgactt cacgctgaac      1140
tcccacgacg cggcgttcaa ggttgagaag ggggagttgc tgtgcgggta ccagccgctg      1200
gtgatgcggg atccagcggt gttcgacgac ccggagacgt tcgccccgga aaggttcatg     1260
ggcagcggga aggagctgct caagtacgtc ttctggtcca acgggccgga gacgggtacg     1320
ccgacgccgc ccaacaagca gtgcgccgcg aaggactacg tggtggagac ggcgtgcctg     1380
ctgatggcgg agatcttcta ccgctacgac gagttcgtgt gcgccgacga cgccatctcc     1440
gtgacgaagc tggatagagc gagagaatgg gagtaaacgg tattcaagtc ggaagcgaca     1500
taaggagacg gccaactcca ccgttgctaa ttcaagtcgt actccaaatc ggtattcata     1560
tcatcgttcc attggggtga tgaagagata aataaaattt gacgttgcag gaggctacaa    1620
aaaaaaaaaa aaaaaaaa                                                    1638

<210> SEQ ID NO 13
<211> LENGTH: 11
<212> TYPE: PRT
<213> ORGANISM: Psidium Guajava (guava)

<400> SEQUENCE: 13

Asp Gly Asn Ala Ser Val Ile Phe Pro Leu Gln
 1               5                  10
```

```
<210> SEQ ID NO 14
<211> LENGTH: 7
<212> TYPE: PRT
<213> ORGANISM: Psidium Guajava (guava)

<400> SEQUENCE: 14

Asn Phe Ala Met Asp Ile Leu
  1               5

<210> SEQ ID NO 15
<211> LENGTH: 7
<212> TYPE: PRT
<213> ORGANISM: Psidium Guajava (guava)

<400> SEQUENCE: 15

Phe Leu Phe Asn Phe Leu Ser
  1               5

<210> SEQ ID NO 16
<211> LENGTH: 27
<212> TYPE: DNA
<213> ORGANISM: Artificial Sequence
<220> FEATURE:
<223> OTHER INFORMATION: Description of artificial sequence:
      /note=synthetic construct

<400> SEQUENCE: 16
gcggatccgg ccatgagcaa catgtcg                                27

<210> SEQ ID NO 17
<211> LENGTH: 21
<212> TYPE: DNA
<213> ORGANISM: Artificial Sequence
<220> FEATURE:
<223> OTHER INFORMATION: Description of artificial sequence:
      /note=synthetic construct

<400> SEQUENCE: 17
aatgttgatg gtggggagga g                                      21

<210> SEQ ID NO 18
<211> LENGTH: 26
<212> TYPE: DNA
<213> ORGANISM: Artificial Sequence
<220> FEATURE:
<223> OTHER INFORMATION: Description of artificial sequence:
      /note=synthetic construct

<400> SEQUENCE: 18
gcggatccgg ccatgtcgcc ggccat                                 26

<210> SEQ ID NO 19
<211> LENGTH: 27
<212> TYPE: DNA
<213> ORGANISM: Artificial Sequence
<220> FEATURE:
<223> OTHER INFORMATION: Description of artificial sequence:
      /note=synthetic construct

<400> SEQUENCE: 19
gcggatccgg ccatgtcgtc cacctac                                27

<210> SEQ ID NO 20
<211> LENGTH: 8
<212> TYPE: PRT
<213> ORGANISM: Psidium Guajava (guava)
```

```
<400> SEQUENCE: 20

Thr Tyr Pro Pro Ser Leu Ser Pro
 1               5

<210> SEQ ID NO 21
<211> LENGTH: 10
<212> TYPE: PRT
<213> ORGANISM: Psidium Guajava (guava)

<400> SEQUENCE: 21

Thr Tyr Pro Pro Ser Leu Ser Pro Pro Ser
 1               5                  10

<210> SEQ ID NO 22
<211> LENGTH: 12
<212> TYPE: PRT
<213> ORGANISM: Psidium Guajava (guava)

<400> SEQUENCE: 22

Thr Tyr Pro Pro Ser Leu Ser Pro Pro Ser Ser Pro
 1               5                  10

<210> SEQ ID NO 23
<211> LENGTH: 13
<212> TYPE: PRT
<213> ORGANISM: Psidium Guajava (guava)

<400> SEQUENCE: 23

Thr Tyr Pro Pro Ser Leu Ser Pro Pro Ser Ser Pro Arg
 1               5                  10

<210> SEQ ID NO 24
<211> LENGTH: 14
<212> TYPE: PRT
<213> ORGANISM: Psidium Guajava (guava)

<400> SEQUENCE: 24

Thr Tyr Pro Pro Ser Leu Ser Pro Pro Ser Ser Pro Arg Pro
 1               5                  10

<210> SEQ ID NO 25
<211> LENGTH: 480
<212> TYPE: PRT
<213> ORGANISM: Capsicum annum (green pepper)

<400> SEQUENCE: 25

Met Ile Pro Ile Met Ser Ser Ala Pro Leu Ser Thr Ala Thr Pro Ile
 1               5                  10                  15

Ser Leu Pro Val Arg Lys Ile Pro Gly Ser Tyr Gly Phe Pro Leu Leu
                20                  25                  30

Gly Pro Leu Trp Asp Arg Leu Asp Tyr Asn Trp Phe Gln Lys Leu Pro
            35                  40                  45

Asp Phe Phe Ser Lys Arg Val Glu Lys Tyr Asn Ser Thr Val Phe Arg
        50                  55                  60

Thr Asn Val Pro Pro Cys Phe Pro Phe Phe Leu Gly Val Asn Pro Asn
 65                  70                  75                  80

Val Val Ala Val Leu Asp Val Lys Ser Phe Ala His Leu Phe Asp Met
                85                  90                  95

Glu Ile Val Glu Lys Ala Asn Val Leu Val Gly Asp Phe Met Pro Ser
                100                 105                 110

Val Val Tyr Thr Gly Asp Met Arg Val Cys Ala Tyr Leu Asp Thr Ser
```

```
                115                 120                 125
Glu Pro Lys His Thr Gln Ile Lys Asn Phe Ser Leu Asp Ile Leu Lys
    130                 135                 140

Arg Ser Ser Lys Thr Trp Val Pro Thr Leu Val Lys Glu Leu Asp Thr
145                 150                 155                 160

Leu Phe Gly Thr Phe Glu Ser Asp Leu Ser Lys Ser Lys Ser Ala Ser
                165                 170                 175

Leu Leu Pro Ala Leu Gln Lys Phe Leu Phe Asn Phe Ser Leu Thr
            180                 185                 190

Phe Leu Gly Ala Asp Pro Ser Ala Ser Pro Glu Ile Ala Asn Ser Gly
            195                 200                 205

Phe Ala Tyr Leu Asp Ala Trp Leu Ala Ile Gln Leu Ala Pro Thr Val
    210                 215                 220

Ser Ile Gly Val Leu Gln Pro Leu Glu Glu Ile Phe Val His Ser Phe
225                 230                 235                 240

Ser Tyr Pro Tyr Phe Leu Val Arg Gly Gly Tyr Glu Lys Leu Ile Lys
                245                 250                 255

Phe Val Lys Ser Glu Ala Lys Glu Val Leu Thr Arg Ala Gln Thr Asp
            260                 265                 270

Phe Gln Leu Thr Glu Gln Glu Ala Ile His Asn Leu Leu Phe Ile Leu
        275                 280                 285

Gly Phe Asn Ala Phe Gly Gly Phe Thr Ile Phe Leu Pro Thr Leu Leu
    290                 295                 300

Gly Asn Leu Gly Asp Glu Lys Asn Ala Glu Met Gln Glu Lys Leu Arg
305                 310                 315                 320

Lys Glu Val Arg Glu Lys Val Gly Thr Asn Gln Glu Asn Leu Ser Phe
                325                 330                 335

Glu Ser Val Lys Glu Met Glu Leu Val Gln Ser Phe Val Tyr Glu Ser
            340                 345                 350

Leu Arg Leu Ser Pro Pro Val Pro Ser Gln Tyr Ala Arg Ala Arg Lys
        355                 360                 365

Asp Phe Met Leu Ser Ser His Asp Ser Val Tyr Glu Ile Lys Lys Gly
    370                 375                 380

Glu Leu Leu Cys Gly Tyr Gln Pro Leu Val Met Lys Asp Pro Lys Val
385                 390                 395                 400

Phe Asp Glu Pro Glu Lys Phe Met Leu Glu Arg Phe Thr Lys Glu Lys
                405                 410                 415

Gly Lys Glu Leu Leu Asn Tyr Leu Phe Trp Ser Asn Gly Pro Gln Thr
            420                 425                 430

Gly Ser Pro Thr Glu Ser Asn Lys Gln Cys Ala Ala Lys Asp Ala Val
        435                 440                 445

Thr Leu Thr Ala Ser Leu Ile Val Ala Tyr Ile Phe Gln Lys Tyr Asp
    450                 455                 460

Ser Val Ser Phe Ser Ser Gly Ser Leu Thr Ser Val Lys Lys Ala Cys
465                 470                 475                 480

<210> SEQ ID NO 26
<211> LENGTH: 483
<212> TYPE: PRT
<213> ORGANISM: Musa sp. (banana)

<400> SEQUENCE: 26

Met Ala Met Met Trp Ser Ser Ala Ser Ala Thr Ala Val Thr Thr Leu
1               5                   10                  15
```

-continued

```
Pro Thr Arg Pro Ile Pro Gly Ser Tyr Gly Pro Pro Leu Val Gly Pro
         20                  25                  30
Leu Lys Asp Arg Leu Asp Tyr Phe Thr Phe Gln Gly Pro Glu Thr Phe
         35                  40                  45
Phe Arg Ser Arg Met Ala Thr His Lys Ser Thr Val Phe Arg Thr Asn
 50                  55                  60
Met Pro Pro Thr Phe Pro Phe Phe Val Gly Val Asp Pro Arg Val Val
 65                  70                  75                  80
Thr Val Leu Asp Cys Thr Ser Phe Ser Ala Leu Phe Asp Leu Glu Val
             85                  90                  95
Val Glu Lys Lys Asn Ile Leu Ile Gly Asp Tyr Met Pro Ser Leu Ser
            100                 105                 110
Phe Thr Gly Asp Thr Arg Val Val Tyr Leu Asp Pro Ser Glu Pro
            115                 120                 125
Asp His Ala Arg Val Lys Ser Phe Cys Leu Glu Leu Leu Arg Arg Gly
130                 135                 140
Ala Lys Thr Trp Val Ser Ser Phe Leu Ser Asn Leu Asp Val Met Leu
145                 150                 155                 160
Ala Thr Ile Glu Gln Gly Ile Ala Lys Asp Gly Ser Ala Gly Leu Phe
                165                 170                 175
Gly Pro Leu Gln Lys Cys Ile Phe Ala Phe Leu Cys Lys Ser Ile Ile
                180                 185                 190
Gly Ala Asp Pro Ser Val Ser Pro Asp Val Gly Glu Asn Gly Phe Val
            195                 200                 205
Met Leu Asp Lys Trp Leu Ala Leu Gln Leu Leu Pro Thr Val Lys Val
            210                 215                 220
Gly Ala Ile Pro Gln Pro Leu Glu Glu Ile Leu Leu His Ser Phe Pro
225                 230                 235                 240
Leu Pro Phe Phe Leu Val Ser Arg Asp Tyr Arg Lys Leu Tyr Glu Phe
                245                 250                 255
Val Glu Lys Gln Gly Gln Glu Val Val Arg Arg Ala Glu Thr Glu His
                260                 265                 270
Gly Leu Ser Lys His Asp Ala Ile Asn Asn Ile Leu Phe Val Leu Gly
            275                 280                 285
Phe Asn Ala Phe Gly Gly Phe Ser Val Phe Pro Thr Leu Leu Thr
            290                 295                 300
Thr Ile Gly Arg Asp Lys Thr Gly Leu Arg Glu Lys Leu Lys Asp Glu
305                 310                 315                 320
Val Arg Arg Val Met Lys Ser Arg Gly Glu Lys Arg Pro Ser Phe Glu
                325                 330                 335
Thr Val Arg Glu Met Glu Leu Val Arg Ser Thr Val Tyr Glu Val Leu
            340                 345                 350
Arg Leu Asn Pro Pro Val Pro Leu Gln Tyr Gly Arg Ala Arg Thr Asp
            355                 360                 365
Phe Thr Leu Asn Ser His Asp Ala Ala Phe Lys Val Glu Lys Gly Glu
            370                 375                 380
Leu Leu Cys Gly Tyr Gln Pro Leu Val Met Arg Asp Pro Ala Val Phe
385                 390                 395                 400
Asp Asp Pro Glu Thr Phe Ala Pro Glu Arg Phe Met Gly Ser Gly Lys
                405                 410                 415
Glu Leu Leu Lys Tyr Val Phe Trp Ser Asn Gly Pro Glu Thr Gly Thr
            420                 425                 430
Pro Thr Pro Ala Asn Lys Gln Cys Ala Ala Lys Asp Tyr Val Val Glu
```

-continued

```
                    435                 440                 445
Thr Ala Cys Leu Leu Met Ala Glu Ile Phe Tyr Arg Tyr Asp Glu Phe
        450                 455                 460
Val Cys Ala Asp Asp Ala Ile Ser Val Thr Lys Leu Asp Arg Ala Arg
465                 470                 475                 480
Glu Trp Glu
```

<210> SEQ ID NO 27
<211> LENGTH: 1464
<212> TYPE: DNA
<213> ORGANISM: Psidium Guajava

<400> SEQUENCE: 27

```
atggcgaggg tcgtgatgag caacatgtcg ccggccatgt cgtccaccta ccccccgtct     60
ctgtccccgc cgtcgtcgcc gcggccgacc accctcccgg tgcggacgat cccgggcagc    120
tacgggtggc cctcctcgg  cccgatatcg gaccgcctgg actacttctg gttccaaggc    180
ccggagacgt tcttcaggaa gaggatcgag aagtacaaga gcaccgtgtt ccgcgcgaac    240
gtgcctccgt gcttcccctt cttctcgaac gtgaagccta acgtcgtggt cgtcctcgat    300
tgcgagtcct tcgctcactt gttcgacatg gagatcgtgg agaagagcaa cgtcctcgtc    360
ggcgacttca tgccgagcgt gaagtacacc gggaacatcc gggtctgcgc ttacctcgac    420
acttccgagc tcaacacgc  tcaggtgaag aactttgcga tggacatact gaagaggagc    480
tccaaagtgt gggagagcga agtgatctcg aacttggaca ccatgtggga caccatcgag    540
tccagcctcg ccaaggacgg caacgccagc gtcatcttcc ctctccaaaa gttcctcttc    600
aacttcctct ccaagtccat catcggcgct gacccggccg cctcgccgca ggtggccaag    660
tccggctacg ccatgcttga ccggtggctc gctctccagc tcctcccac  catcaacatt    720
ggcgtactgc agcctctagt ggagattttt ctgcattctt gggcataccc ttttgcgctg    780
gtgagcgggg actacaacaa gctctaccag ttcatcgaga aggaaggccg agaagcggtc    840
gaaagggcga aggccgagtt cggattgaca caccaggagg ccatccacaa cttgctgttc    900
atcctcggct tcaacgcgtt cggcggcttc tcgatcttcc tccccacgtt gctgagcaac    960
atacttagcg acacaaccgg actgcaggac cggctgagga aggaggtccg ggcaaaggga   1020
gggccggcgt tgagcttcgc ctcggtgaag gagatggaac tcgtgaagtc ggtcgtgtac   1080
gagacgctgc ggctcaaccc gcccgtcccg ttccaatacg ctcgagcccg gaaggacttc   1140
cagctcaagt cccacgactc tgtctttgat gtcaagaaag gcgagctgct atgcgggtat   1200
cagaaggtgg tgatgacaga cccgaaagtg ttcgacgaac cggagagctt caactcggac   1260
cggttcgtcc aaaacagcga gctactggat tacctgtact ggtccaacgg gccgcagacc   1320
ggaacgccga ccgagtcgaa caagcagtgc gcggctaagg actacgtcac cctcaccgct   1380
tgtctcttcg ttgcctacat gtttcgacgg tacaattccg tcagaggaag ctcgagctcg   1440
atcacagccg ttgaaaaggc caac                                          1464
```

GUAVA (PSIDIUM GUAJAVA) 13-HYDROPEROXIDE LYASE AND USES THEREOF

This application is a divisional of and claims the benefit of U.S. Ser. No. 09/578,533, filed May 24, 2000, which is a pending application, and which claims priority to U.S. Ser. No. 09/078,173, filed May 13, 1998, which has issued as U.S. Pat. No. 6,200,794 B1, both of which are incorporated herein by reference in their entirety.

BACKGROUND OF THE INVENTION

1. Field of the Invention

The present invention relates to fatty acid 13-hydroperoxide lyase protein from guava (*Psidium guajava*) and the gene encoding the protein. The present invention also relates to the means for expressing guava 13-hydroperoxide lyase and methods of using guava 13-hydroperoxide lyase in the field of organic synthesis.

2. Background Art

Green notes, which include n-hexanal, hexan-1-ol, 2(E)-hexen-1-al, 2(E)-hexen-1-ol and 3(Z)-hexen-1-ol (also known as pipol), are used widely in flavors, particularly fruit flavors, to impart a fresh green character. Furthermore, green notes are essential for fruit aroma and are used extensively in the aroma industry. The demand for natural green notes has grown to exceed their supply from traditional sources such as mint (*Mentha arvensis*) oil. This has motivated research efforts toward finding alternative natural ways of obtaining these materials.

The synthesis of green note compounds starts from free (polyunsaturated) fatty acids such as linoleic (9(Z), 12(Z)-octadecadienoic) and α-linolenic (9(Z), 12(Z), 15(Z)-octadecatrienoic) acids. In nature, these acids are released from cell membranes by lipolytic enzymes after cell damage. Fatty acid 13-hydroperoxides are formed by the action of a specific lipoxygenase (13-LOX) and are subsequently cleaved by a specific 13-hydroperoxide lyase (13-HPOL) into a C-6 aldehyde and a C-12 ω-oxoacid moiety.

The aldehydes can subsequently undergo thermal isomerization and/or be reduced by dehydrogenase enzymes to give the other C-6 products (i.e., green notes) mentioned above (Hatanaka, 1993; Hatanaka, et al., 1987).

The enzyme 13-HPOL has proven difficult to study because it is membrane bound and is present in only small quantities in plant tissue. It was identified for the first time in banana fruits (Tressl and Drawert, 1973) and was subsequently studied in a number of different plant materials, including watermelon seedlings (Vick and Zimmerman, 1976), apple and tomato fruits (Schreier and Lorenz, 1982), tomato leaves (Fauconnier et al., 1997), cucumber seedlings (Matsui, et al, 1989), and soybean seedlings (Olias et al., 1990). The enzyme has been purified to apparent homogeneity from tea leaves (Matsui et al., 1991) and, more recently, from green bell pepper fruits (Shibata et al., 1995), tomato leaves (Fauconnier et al., 1997), and banana (European Patent Application, Publication No. EP 0801133 A2). The various characteristics of 13-HPOLs that have been studied are summarized in Table 1.

TABLE 1

Summary of the Properties of 13-HPOL from Different Sources

| Enzyme Source | Native Mass (kD) | Sub-Unit Structure | Structure | pH Optimum | pI |
|---|---|---|---|---|---|
| Cucumber | — | — | — | 8.0 | — |
| Green pepper | 170 | 55 | Trimer | — | — |
| Soybean seedlings | 240–260 | 62 | Tetramer | 6.0–7.0 | — |
| Tea leaves | — | 53 and 55 | — | 7.5 | — |
| Tomato fruits | 200 | — | — | 5.5 | 5.8–6.1 |
| Watermelon | >250 | — | — | 6.0–6.5 | — |
| Tomato leaves | 216 | 73 | Trimer | 7.0 | 4.9 |

Guava has recently been identified as an excellent source of freeze-stable 13-HPOL for use in this synthetic pathway. Guava 13-HPOL is currently used in an industrial process for the production of green notes (U.S. Pat. No. 5,464,761). In this process, a solution of the required 13-hydroperoxides is made from linoleic or linolenic acid (obtained from sunflower and linseed oils, respectively) using freshly prepared soybean flour as a source of 13-LOX. This solution is then mixed with a freshly prepared puree of whole guava (*Psidium guajava*) fruit, as the source for 13-HPOL. The aldehyde products are then isolated by distillation. When the alcohols are required, fresh baker's yeast is added to the hydroperoxide solution before it is mixed with the guava puree. This yeast contains an active alcohol dehydrogenase enzyme that reduces the aldehydes as they are formed by 13-HPOL.

There are a number of disadvantages to this industrial process. The principal disadvantage is the requirement of large quantities of fresh guava fruit. Such a requirement means that the process has to be operated in a country where fresh guava fruit is cheaply and freely available. Even when such a site is found, availability is limited to the growing season of the fruit. Good quality guava fruit, for example, is only available for ten months of the year in Brazil.

A second disadvantage is that the desired enzyme activities are rather dilute in the sources employed. This means that relatively large amounts of soy flour (5%), guava puree (41%) and yeast (22%) have to be used in the process. The large volumes of these crude materials that are required for industrial production place physical constraints on the yields of green notes that can be achieved.

A third disadvantage is that it is a large-volume batch process, which, by its nature, does not make maximum use of the 13-HPOL enzyme's catalytic activity, is relatively labor intensive and generates a large amount of residual organic material. The residual organic material must subsequently be transported to a compost farm or otherwise discarded.

The present invention overcomes these limitations and disadvantages related to the source of guava 13-HPOL by providing purified and recombinant guava 13-HPOL proteins, nucleic acids, expression systems, and methods of use thereof.

SUMMARY OF THE INVENTION

The present invention provides a fatty acid 13-hydroperoxide lyase (13-HPOL) and a nucleic acid encoding the lyase. In particular, it provides a guava-derived protein having 13-hydroperoxide lyase function and a nucleic acid encoding such protein. The present invention further provides a nucleic acid which specifically hybridizes with the nucleic acid encoding guava 13-hydroperoxide lyase under stringent conditions and which does not hybridize at the same stringent conditions to the nucleic acid encoding green pepper or banana 13-hydroperoxide lyase.

The present invention also provides means for expressing recombinant 13-hydroperoxide lyase. Specifically, a vector for the expression of a guava 13-hydroperoxide lyase comprising the nucleic acid of the present invention and cells containing the exogenous nucleic acid of the present invention are provided. Also provided is a method of expressing the recombinant protein produced by the transformed cells comprising optimizing active lyase function of the recombinant protein.

The present invention further provides methods of using recombinant 13-hydroperoxide lyase. Specifically, the present invention provides a method of cleaving a 13-hydroperoxide of linoleic acid into a n-hexanal and a $C_{12}$-oxocarboxylic acid. Also provided is a method of preparing n-hexanal, 3-(Z)-hexen-1-al, 2-(E)-hexen-1-al, or their corresponding alcohols from 13-hydroperoxy-octadeca-9,11-dienoic acid or 13 hydroperoxy-octadeca-9,11,15-trienoic acid.

BRIEF DESCRIPTION OF THE DRAWINGS

Figure 1A:
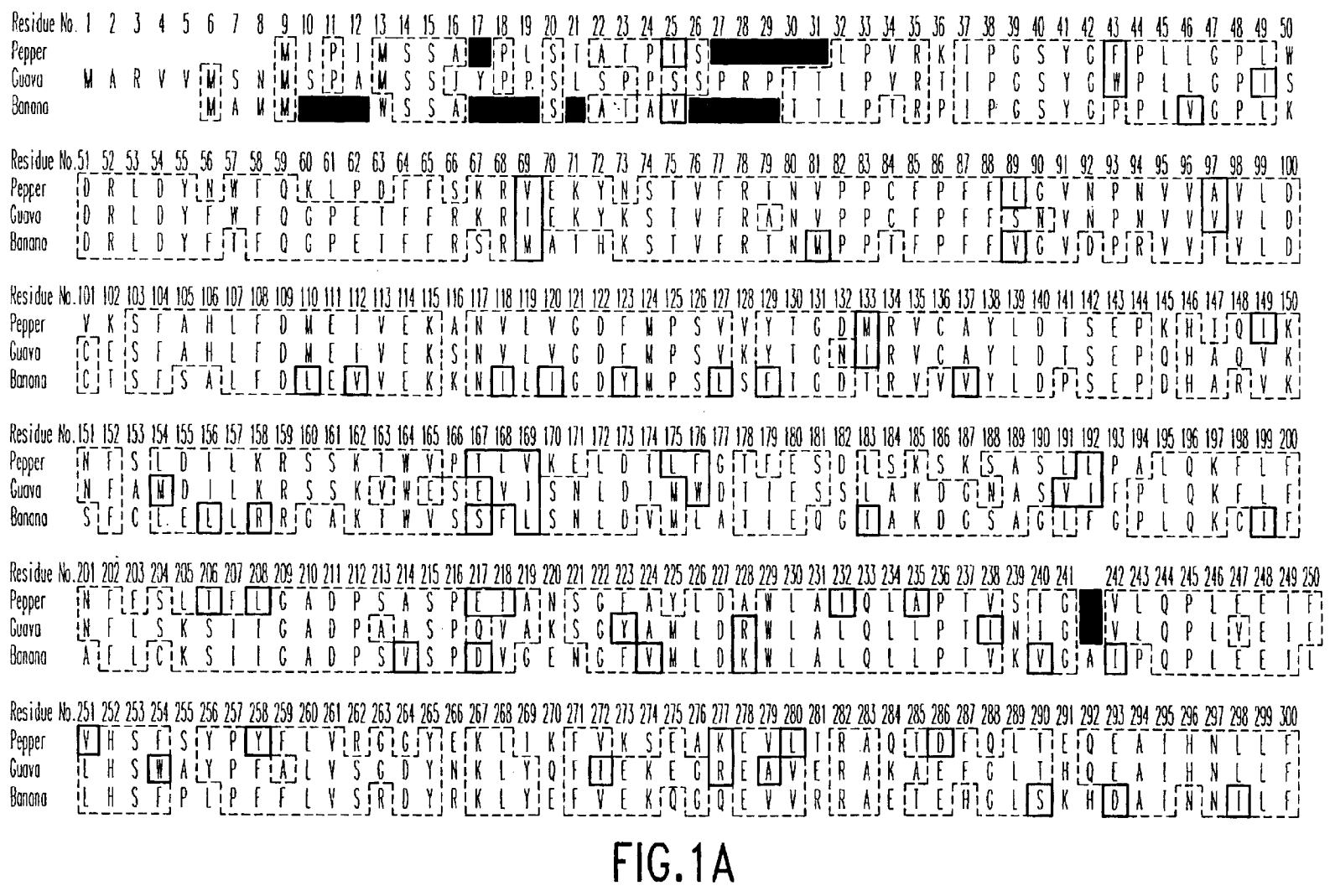

FIGS. 1A and 1B together show the alignment of derived full length amino acid sequence for guava (SEQ ID NO:6), green pepper (SEQ ID NO:25), and banana (SEQ ID NO:26) 13-hydroperoxide lyases. The numbering system used is that of guava 13-hydroperoxide lyase. Amino acid residues that are identical in all three sequences are indicated by boxes with dashed lines. Similar amino acids are indicated by boxes with solid lines. Start sites are indicated by bold text. Deletions/insertions are indicated by solid black boxes.

FIGS. 2A and 2B together show the complete cDNA sequence (SEQ ID NO:27) and derived amino acid sequence (SEQ ID NO:6) for guava 13-hydroperoxide lyase. The Met-1, Met-6, Met-9, and Met-13 start sites are indicated. Also indicated are peptides that correspond to the HPLC peaks 12, 13, and 15, and the cysteine of the heme binding site at residue 450.

DETAILED DESCRIPTION OF THE INVENTION

Figure 1B:
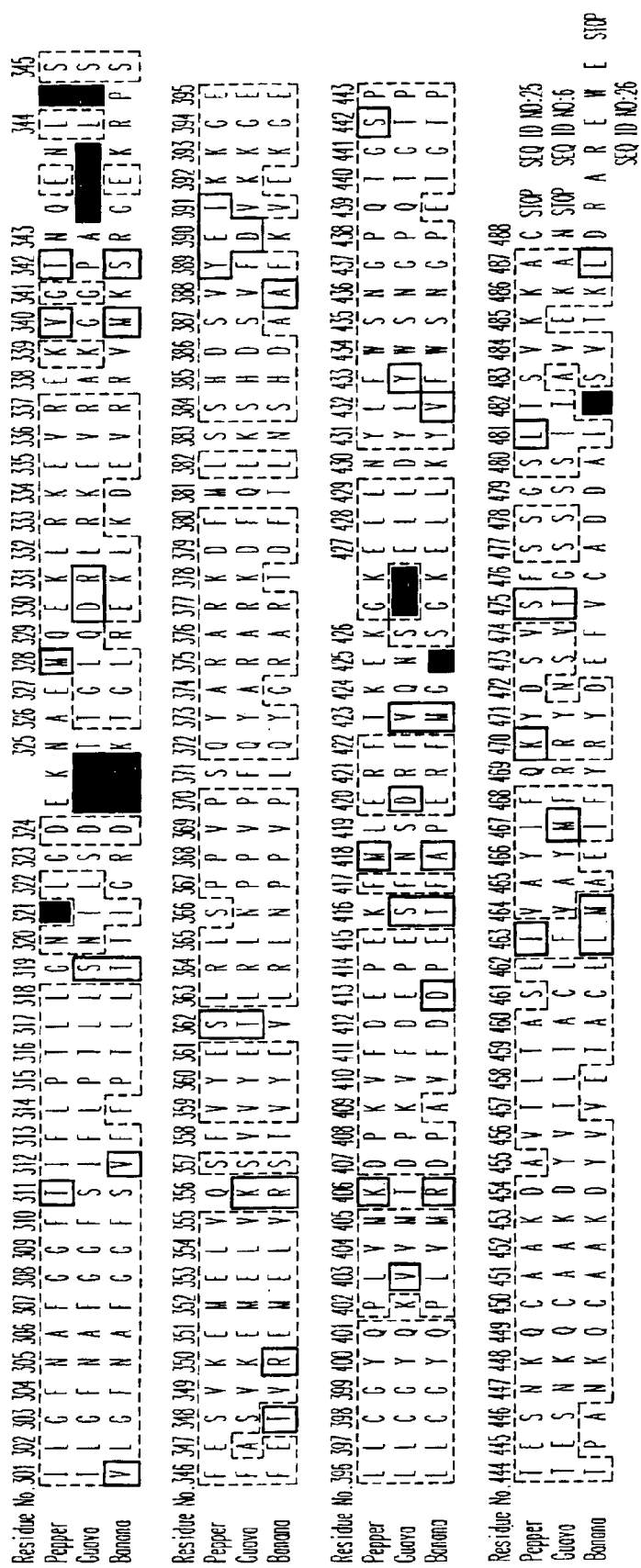

As used in the specification and in the claims, "a" can mean one or more, depending upon the context in which it is used.

The present invention provides a guava fatty acid 13-HPOL and a nucleic acid encoding the lyase. In particular, it provides a guava-derived protein having 13-HPOL function and a nucleic acid encoding such polypeptide or protein. The term "protein" refers to a polymer of amino acids and can include full-length proteins and polypeptides and fragments thereof.

In the present invention, "lyase" means a protein having at least one lyase function. In particular, the term "13-hydroperoxide lyase" and "functional 13-hydroperoxide lyase" means a lyase protein having at least one function exhibited by native 13-hydroperoxide lyase. For example, 13-HPOL function can include the catalytic activity of cleaving a fatty acid 13-hydroperoxide into a C-6 aldehyde and a C-12-ω-oxoacid moiety. Additionally, the protein can have the following characteristics of 13-HPOL: antigenic determinants, binding regions, or the like. A lyase can comprise additional amino acids, such as amino acids linked to the N-terminal end, or amino acids linked to the C-terminal end or amino acids inserted within the lyase sequence, as long as the resulting protein or peptide retains a lyase function.

The 13-HPOL was purified to apparent homogeneity from guava fruit, and the nucleotide sequence for the full-length gene was determined to be 1467 base pairs (SEQ ID NO:10). The translated sequence encodes a total of 488 amino acids (SEQ ID NO: 6), corresponding to a protein with a calculated molecular weight of 54,817 Daltons, a molar extinction coefficient (at 280 nm) of 63,590±5% and an isoelectric point of 7.29.

As shown in FIG. 1, the derived full length amino acid sequence shows a degree of homology to the 13-HPOL gene that was recently cloned from green pepper (*Capsicum annuum*) (Matsui et al., *FEBS Lett.*, 1996) and banana (Musa sp.) (European Patent Application, Publication No. EP 081133 A2). Taking into account deletions and insertions, the alignment reveals that, of the amino acids that overlap with the green pepper sequence (480), 324 are identical and a further 40 are similar (similar amino acids are S, T; D, E; N, Q; R, K; I, L, M, A, V; F, Y, W; whereas G, C, P and H are not considered to have equivalents). This means that the green pepper amino acid sequence and the full length guava amino acid sequence have an identity (homology) of only approximately 67% and a similarity of only approximately 76%. Of the amino acids that overlap with the banana sequence (483), 280 are identical and a further 48 are similar. This means that the banana and guava sequences have an identity (homology) of only approximately 58% and a similarity of only approximately 68%.

There are significant differences between the guava 13-HPOL and the green pepper and banana 13-HPOLs (FIG. 1). Comparison of the amino acid sequences for the three proteins shows that both the pepper and banana sequences are shorter than the full length guava sequence. Moreover, the guava gene contains four possible start sites within the first 13 amino acids (methionines 1, 6, 9 and 13), whereas the pepper sequence has only two, corresponding to guava-Met9 and guava-Met13, and the banana sequence has three, one at residue 8 and two corresponding to guava-Met6 and guava-Met9. In addition, the guava sequence contains a unique region at residues 16-22 (T Y P P S L S) (SEQ ID NO: 1), which both the green pepper and banana sequences lack. The unique region can further include residues 16-23 (T Y P P S L S P) (SEQ ID NO: 20); 16-25 (T Y P P S L S P P S)(SEQ ID NO: 21); 16-27 (T Y P P S L S P P S S P) (SEQ ID NO: 22); 16-28 (T Y P P S L S P P S S P R) (SEQ ID NO: 23); 16-29 (T Y P P S L S P P S S P R P) (SEQ ID NO: 24). In addition, other amino acid and nucleotide sequences encoding 13-HPOL are unique to guava.

Thus, the present invention provides an isolated protein comprising a fatty acid 13-hydroperoxide lyase comprising the amino acid sequence set forth in SEQ ID NO:1, i.e., comprising the amino acid residues found at residues 16-22 of the guava 13-HPOL. The lyase, in addition to having the amino acid residues set forth in SEQ ID NO: 1, can comprise additional amino acid residues so long as the protein retains its lyase function. Examples of such lyases include the fatty acid 13-hydroperoxide lyase isolated from *Psidium guajava*, such as those set forth in SEQ ID NO:2 (guava 13-HPOL Met13), SEQ ID NO:3 (guava 13-HPOL Met9), SEQ ID NO:4 (guava 13-HPOL Met6), and SEQ ID NO:6 (guava 13-HPOL Met1).

It should be noted that active lyase enzyme is obtained upon expression of the guava protein with the sequence including all four of the methionines (guava-Met1), or with the shorter sequences including three (guava-Met6), two (guava-Met9), or only one methionine (guava-Met13). Enzyme activity is three-fold higher when only two (guava-Met9) or one (guava-Met13) methionines are included in the expressed protein.

The present invention additionally provides a fatty acid 13-hydroperoxide lyase comprising at its N-terminus the first eight amino acids of the guava 13-HPOL, i.e., the amino acid sequence set forth in SEQ ID NO:5. For example, the invention provides a protein having the amino acid sequence set forth in SEQ ID NO:6. The term "at its N-terminus" refers to the amino acid residues at the amino terminus of the full length lyase, wherein there may be additional residues attached to the amino terminus of the full length protein. More specifically, the amino acid sequence of the fatty acid 13-hydroperoxide lyase with the amino acid sequence of SEQ ID NO:5 at its N-terminus can be an amino acid sequence present in fatty acid 13-hydroperoxide lyase isolated from *Psidium guajava*.

As will be appreciated by those skilled in the art, the invention also includes those proteins having slight variations in amino acid sequences or other properties. Such variations may arise naturally as allelic variations (e.g., due to genetic polymorphism) or may be produced by human intervention (e.g., by mutagenesis of cloned DNA sequences), such as induced point, deletion, insertion and substitution mutants. When such variations occur, minor changes in amino acid sequence are generally preferred, such as conservative amino acid replacements, small internal deletions or insertions, and additions or deletions at the ends of the molecules. Substitutions may be designed based on, for example, the model of Dayhoff, et al., 1978. These modifications can result in changes in the amino acid sequence, provide silent mutations, modify a restriction site, or provide other specific mutations.

The present invention further provides isolated nucleic acids comprising nucleic acids encoding the proteins of the present invention. For example, the nucleic acid set forth herein as SEQ ID NO: 7 provides a nucleotide sequence for a nucleic acid that encodes the 13-HPOL comprising the amino acid set forth in SEQ ID NO:1, i.e., comprising the amino acid residues found at residues 16-22, 16-23, 16- 25, 16-27, 16-28, or 16-29 of the guava 13-HPOL and, more specifically, the guava 13-HPOL Met13 as set forth in SEQ ID NO:2. Other examples of such nucleic acids are the nucleic acids having the nucleotide sequence set forth herein as SEQ ID NO:8, which encodes the guava 13-HPOL Met9 set forth in SEQ ID NO: 3 and SEQ ID NO:9, which encodes the guava 13-HPOL Met6 set forth as SEQ ID NO:4. Yet another example is SEQ ID NO:10, which encodes the protein comprising a fatty acid 13-HPOL comprising at its N-terminus the amino acid sequence set forth in SEQ ID NO:5 and more specifically the guava 13-HPOL Met 1 as set forth in SEQ ID NO:6. Additional nucleic acids encoding these proteins can readily be made, utilizing the degeneracy of the genetic code. Additionally, a nucleic acid encoding any selected protein can readily be made, based upon the genetic code, as known in the art. Nucleic acids can be obtained by any of several means known in the art. For example, cDNAs can be isolated from a library using a probe derived from the present nucleic acids or polypeptides, or nucleic acids can be directly synthesized mechanically. The nucleic acids can be double or single-stranded depending upon the purpose for which it is intended.

The present invention further provides an isolated nucleic acid which specifically hybridizes with the nucleic acid of SEQ ID NO:7 (i.e., the nucleotide sequence encoding guava 13-HPOL Met13 as set forth in SEQ ID NO:2) under stringent conditions of hybridization and which does not hybridize at the stringent conditions to the nucleic acid set forth in SEQ ID NO:11 (i.e., the nucleotide sequence of green pepper 13-HPOL) or SEQ ID NO:12 (i.e., the nucleotide sequence of banana 13-HPOL). Preferably, the isolated nucleic acid has at least 99, 98, 97, 95, 90, 85, 80, 75, or 70% complementarity with the sequence to which it hybridizes. More preferably, the isolated nucleic acid encodes a functional 13-HPOL. The nucleic acid can also be a probe or a primer, for example, to detect or amplify target nucleic acids. Typically, a unique nucleic acid useful as a primer or probe will be at least about 20 to about 25 nucleotides in length, depending upon the specific nucleotide content of the sequence. Additionally, fragments can be, for example, at least about 30, 40, 50, 75, 100, 200, or 500 nucleotides in length. Alternatively, a full length sequence or a sequence that is longer than a full length sequence can be used.

"Stringent conditions" refers to the hybridization conditions used in a hybridization protocol or in the primer/template hybridization in a PCR reaction. In general, these conditions should be a combination of temperatures and salt concentrations for washing chosen so that the denaturation temperature is approximately 5–20° C. below the calculated $T_m$ (melting/denaturation temperature) of the hybrid under study. The temperature and salt conditions are readily determined empirically in preliminary experiments in which samples of reference nucleic acid are hybridized to the primer nucleic acid of interest and then amplified under conditions of different stringencies. The stringency conditions are readily tested and the parameters altered are readily apparent to one skilled in the art. For example, $MgCl_2$ concentrations used in PCR buffer can be altered to increase the specificity with which the primer binds to the template, but the concentration range of this compound used in hybridization reactions is narrow, and therefore, the proper stringency level is easily determined. For example, hybridizations with oligonucleotide probes 18 nucleotides in length can be done at 5–10° C. below the estimated $T_m$ in 6×SSPE, then washed at the same temperature in 2×SSPE. The $T_m$ of such an oligonucleotide can be estimated by allowing 2° C. for each A or T nucleotide, and 4° C. for each G or C. An 18 nucleotide probe of 50% G+C would, therefore, have an approximate $T_m$ of 54° C. Likewise, the starting salt concentration of an 18 nucleotide primer or probe would be about 100–200 mM. Thus, stringent conditions for such an 18 nucleotide primer or probe would be a $T_m$ of about 54° C. and a starting salt concentration of about 150 mM and modified accordingly by preliminary experiments. $T_m$ values can also be calculated for a variety of conditions utilizing commercially available computer software (e.g., OLIGO®).

Modifications to the nucleic acids of the invention are also contemplated as long as the essential structure and function of the protein encoded by the nucleic acids is maintained. Likewise, fragments used as primers can have substitutions, so long as enough complementary bases exist for selective amplification, and fragments used as probes can have substitutions, so long as enough complementary bases exist for hybridization with the reference sequence to be distinguished from hybridization with other sequences.

Probes of this invention can be used, for example, to screen genomic or cDNA libraries or to identify complementary sequences by Northern and Southern blotting.

Primers of this invention can be used, for example, to transcribe cDNA from RNA and to amplify DNA according to standard amplification protocols, such as PCR, which are well known in the art.

The present invention also provides vectors for the expression of a *Psidium guajava* 13-hydroperoxide lyase comprising the nucleic acids of the present invention. More specifically, the vector can be a plasmid. Even more specifically, the vector can comprise a promoter functionally linked to one of the nucleic acids of the present invention. "Vector" means any carrier containing foreign DNA. "Vectors" include but are not limited to plasmids, viral nucleic acids, viruses, phage nucleic acids, phages, cosmids, and artificial chromosomes. The vector will typically contain appropriate sequences for expression of the 13-HPOL.

The present invention also provides cells containing an exogenous nucleic acid comprising one of the nucleic acids of the present invention. More specifically, the cell can be an *Escherichia coli* or yeast cell.

The present invention also provides a method of cleaving a 13-hydroperoxide of linoleic acid or α-linolenic acid into a $C_6$-aldehyde and a $C_{12}$-oxocarboxylic acid comprising contacting the recombinant protein produced by the vector of the present invention with the 13-hydroperoxide, thereby cleaving the 13-hydroperoxide.

Further provided is a method of preparing n-hexanal, 3-(Z)-hexen-1-al, 2-(E)-hexen-1-al, or their corresponding alcohols from 13-hydroperoxy-octadeca-9,11-dienoic acid (13-HPOD) or 13 hydroperoxy-octadeca-9,11,15-trienoic acid (13-HPOT), comprising contacting the 13-hydroperoxy-octadeca-9,11-dienoic acid or the 13 hydroperoxy-octadeca-9,11,15-trienoic acid with the recombinant protein produced by the vector of the claimed invention, thereby converting the 13-hydroperoxy-octadeca-9,11-dienoic acid into n-hexanal or the 13 hydroperoxy-octadeca-9,11,15-trienoic acid into 3-(Z)-hexen-1-al; and either recovering the n-hexanal or 3-(Z)-hexen-1-al; reducing the n-hexanal into n-hexanol or the 3-(Z)-hexen-1-al into 3-(Z)-hexen-1-ol and recovering the hexanol or 3-(Z)-hexen-1-ol; or isomerizing the 3-(Z)-hexen-1-al under temperature and pH conditions effective to obtain 2-(E)-hexen-1-al and either recovering the formed 2-(E)-hexen-1-al or reducing the 2-(E)-hexen-1-al to 2-(E)-hexen-1-ol and recovering the 2-(E)-hexen-1-ol from the medium.

Also provided is a method of expressing a recombinant protein produced by the transformed cell of the invention, comprising optimizing active lyase function of the recombinant protein by culturing the cells in the absence of isopropyl β-D-thiogalactopyranoside. Active lyase function can be further optimized by culturing the cells in the absence of a heme precursor, including, for example, δ-aminolevulinic acid. Active lyase function can be even further optimized by culturing the cells for greater than 24 hours and, preferably, for 48 hours at approximately 20–30° C., and more preferably at 23° C.

EXAMPLES OF THE INVENTION

The present invention is more particularly described in the following examples, which are intended as illustrative only since numerous modifications and variations therein will be apparent to those skilled in the art.

Example 1

Purification of Guava 13-HPOL

Methods

Materials

Unless otherwise stated all chemicals were purchased from Fluka and all HPLC columns were purchased from Pharmacia. Pectinex Ultra SP-L was from Novo Nordisk Ferment. Immobilon CD membranes were from Millipore. Quick-Stain was obtained from Zoion Research Inc.

SDS-PAGE

SDS-PAGE with 6.5 or 10% separating gels was done with the buffer system of Laemmli (1970). The gels were stained with Coomassie blue.

Protein Determination

Protein concentrations were determining using the dye-binding method of Bradford (1976).

Enzyme Assays

13-Hydroperoxides from solubilized linolenic and linoleic acids were produced with soybean 13-HPOL (type V, Sigma) according to the method of Vick (1991). During the purification, 13-HPOL activity was measured by following the decrease in absorption at 234 nm, which represents the disruption of the conjugated diene system in the fatty acid hydroperoxide substrate. The assay contained 100 μM of fatty acid 13-hydroperoxide in 1 ml of 100 mM potassium phosphate buffer at pH 6.0 (Vick, 1991).

Although the above assay was convenient, it did not discriminate between 13-HPOL and other enzymes that consume the 13-hydroperoxides, i.e. allene oxide synthase (AOS) (Song and Brash, 1991; Song et al., 1993). Another more specific assay for 13-HPOL was used to confirm that the correct enzyme was purified. This coupled assay used alcohol dehydrogenase and NADH to reduce the aldehydes from the lyase reaction to alcohols. This consumed the NADH and resulted in a decrease in absorption at 340 nm (Vick, 1991).

To verify that the purified enzyme was 13-HPOL, the purified enzyme (50 μl) was incubated for 30 min in 100 mM potassium phosphate buffer pH 6.0 (5 ml) containing 60 μM 13-(S)-Hydroperoxy-9(Z), 11(E)-octadecadienoic acid (13-HPOD) or 13-(S)-Hydroperoxy-9(Z), 11(E), 15(Z)-octadecatrienoic acid (13-HPOT). Volatiles were extracted twice with 1.5 ml diethyl ether. After concentrating the volume to 400 μl under a stream of nitrogen, 1 μl was analyzed by both GC (Supelcowax 10, 15 m, 0.53 mm ID column with a temperature gradient 50 to 120° C. at 5° $min^{-1}$) and GC-MS. Preparations containing 13-HPOL activity were stored frozen at −20° C. and neutral pH between each column step.

The non-volatile C-12 fragment was analyzed by radio-HPLC. Accordingly, [$^{14}$C]-13-(S)-hydroperoxylinoleic acid (52 mCi/mmole) was incubated as above with a sample of the purified enzyme for 5 min and the products were analyzed on an Ultrasphere $C_{18}$ column (5μ, 6.4×250 mm) using $CHCN:H_2O$:acetic acid (glacial) (60:40:0.01, 1.1 ml/min) as solvent. The results showed that the major polar product had a retention time compatible with that expected of 12-oxo-9(Z)-dodecenoic acid and not that of the characteristic α-ketol derivative formed by plant AOSs.

Purification Techniques

Guava fruits were peeled and the pericarp (fleshy) tissue chopped into small pieces. Two volumes of extraction buffer (50 mM sodium phosphate, 1% Triton X-100R, 5 mM sodium ascorbate, pH 7.0) were added to 500 g of chopped pericarp and homogenized for 2 min in a Sorvall mixer at 4° C. The slurry was stirred for 30 min at 4° C. After centrifugation at 16,000×g for 15 min, 0.02% Pectinex Ultra SP-L solution was added to destroy pectin, and the slurry was stirred for a further 30 min at room temperature to give a preparation referred to as the crude extract (1,600 ml).

Solid $(NH_4)_2SO_4$ was added in small portions to the crude extract at 4° C. under stirring until 30% saturation was achieved. After stirring for a further 30 min, the mixture was centrifuged at 20,000×g for 15 min and the resulting pellet discarded. The supernatant was brought to 60% saturation with more solid $(NH_4)_2SO_4$ added in portions. After stirring for 30 min, the pellet was collected by centrifugation as above. The $(NH_4)_2SO_4$ pellet was dissolved in a minimal volume of extraction buffer (45 ml) and chromatographed (5 runs, maximal loading volume 9 ml) on a Superdex 200 HL 26/60 FPLC gel permeation (GPC) column with 50 mM sodium phosphate, 0.1% Triton X-100R, pH 7.0 as running buffer. The flow used was 2 ml $min^{-1}$, and one fraction was collected every 2 min. Fractions with 13-HPOL activity (eluting between 75 ml and 85 ml of the run volume) were pooled.

The combined fractions were brought to 30% $(NH_4)_2SO_4$ saturation before loading onto a Phenyl-Sepharose HR 26/10 hydrophobic interaction (HIC) column with loading buffer (50 mM sodium phosphate, 1 M $(NH_4)_2SO_4$, pH 7.0). 13-HPOL was eluted with a decreasing salt gradient (100–0% over 70 min) with 50 mM sodium phosphate (pH 7.0) containing 0.1% Triton X-100R. The flow used was 8 ml $min^{-1}$ and one fraction was collected each minute. The fractions with 13-HPOL activity (F20–33) were pooled, concentrated by dialysis against polyethylene glycol 20,000 and then de-salted on a PD-10 column (Pharmacia) against the loading buffer (10 mM sodium phosphate, 0.1% Triton X-100R, pH 6.8) for hydroxyapatite chromatography.

The prepared sample was applied to an Econo-Pac HTP column (Biorad). 13-HPOL activity was eluted with a gradient from 0–50% of 400 mM sodium phosphate buffer (pH 6.8), containing 0.1% Triton X-100R over 30 min. The flow was 1 ml $min^{-1}$, and one fraction $min^{-1}$ was collected. Fractions with 13-HPOL activity (F13-24) were pooled, concentrated by dialysis against polyethylene glycol 20,000 and then desalted against a loading buffer (75 mM Tris-acetic add, pH 9.3) suitable for isoelectric focusing chromatography (IFC). The prepared sample was applied to a Mono P HR 5/20 column. 13-HPOL activity was eluted with 10% Polybuffer 96—acetic add, pH 6.0. The flow used was 0.5 ml $min^{-1}$. One fraction was collected every 2 min.

Results

The results of the purification steps are summarized in Table 2.

TABLE 2

Purification of 13-HPOL from Guava Fruit

| Purification Step | Total Protein (mg) | Total 13-HPOL Activity (nkat) | Recovered Activity (%) | Specific 13-HPOL Activity (nkat $mg^{-1}$) | Purification Factor |
|---|---|---|---|---|---|
| Crude extract | 1,111 | 172,050 | 100.0 | 155 | — |
| 30–60% $(NH_4)_2SO_4$ pellet | 762 | 62,300 | 36.2 | 82 | — |
| GPC | 39 | 32,640 | 19.0 | 837 | 5.4 |
| HIC | 16 | 15,160 | 8.8 | 947 | 6.1 |
| Hydroxylapatite | 1.6 | 6,500 | 3.8 | 4,062 | 26.2 |
| IFC | 0.03 | 317 | 0.2 | 10,566 | 68.2 |

SDS-PAGE analysis of samples from the purification showed that the sample after the chromatofocusing step contained just one, apparently homogenous, band with an apparent molecular weight of 50 kD.

The results from the GPC step indicated that the guava 13-HPOL had a molecular mass of 200 kD. This result, when taken together with the SDS-PAGE analysis of subunit size (50 kD), suggests that the enzyme is a homotetramer. This structure is consistent with data reported for soybean 13-HPOL but inconsistent with data for the enzyme from green pepper fruits and tomato, indicating that the enzymes from green pepper and tomato are trimeric.

The 13-HPOL purified from guava fruit tissue had a broad pH optimum of around 6.0–8.0 and a pI of 6.8 as determined by chromatofocusing.

Example 2

Tryptic Digest and Amino Acid Sequence Determination

Methods

Fractions of purified 13-HPOL were concentrated and then separated on a 6.5% SDS-polyacrylamide gel. Following electrophoresis the proteins were electrotransferred to an ImmobilonCD membrane using a transfer buffer consisting of 10 mM CAPS containing 10% (v/v) methanol pH 11.0. Transfer was achieved in 75 min using a current of 0.8 mA $cm^{-2}$. Proteins were detected by staining using Quick-Stain according to the manufacturer's instructions.

Direct N-Terminal sequencing of the purified 13-HPOL sub-units by Edman degradation was not possible as the ends were blocked. The protein band, therefore, was cut out and incubated in 10 µl of 0.1 M Tris pH 8.2 containing 1 M NaCl, 10% (v/v) acetonitrile, 2 mM $CaCl_2$ and 0.1 µg trypsin (which cleaves specifically on the carbonyl side of lysine- and arginine-containing peptide linkages) at 37° C. for 15 h. After acidification with 1 µl of 10% TFA the solution was injected directly onto the HPLC system (RP-300 column, Brownlee). Chromatography solvents were 0.05% TFA and 2% acetonitrile in water (solvent A) and 0.045% TFA and 80% acetonitrile in water (solvent B). The gradient and flow used were 0–5 min 80 µl $min^{-1}$ at 2% solvent B; 5–65 min 50 µl $min^{-1}$ at 2–65% solvent B, and 65–70 min 50 µl $min^{-1}$ $at$ 65–100% B. $A_{214}$ was measured in a 200 nl flow cell with a path length of 2 mm. The HPLC-MS interface and post column flow splitting are described in Hess et al., 1993. HPLC-separated peptides were collected manually for sequence analysis and applied to pre-cycled polybrene-treated glass fiber discs. Automated sequencing was done on a model 477A pulsed-liquid phase sequencer (Applied Biosystems, Foster City, Calif.) equipped with a model 120A analyser.

Results

The following amino acid sequence information was obtained for three individual peptides represented by peaks 12, 13 and 15 of the HPLC analysis: Peak Number 12:    Asp-Gly-Asn-Ala-Ser-Val-Ile-Phe-Pro-Leu-Gln    (SEQ ID NO: 13);

Peak Number 13:    Asn-Phe-Ala-Met-Asp-Ile-Leu    (SEQ ID NO: 14);

Peak Number 15:    Phe-Leu-Phe-Asn-Phe-Leu-Ser    (SEQ ID NO: 15).

Example 3

Determination of the Nucleotide and Derived Amino Acid Sequences of Guava 13-HPOL Methods General DNA Manipulation Methods All media preparation, agarose gel electrophoresis, and general cloning methods were carried out according to standard methods widely known in the art (*Molecular Cloning*, eds. Sambrook, Fritsch, and Maniatis, 1989) unless otherwise stated. QIAprep plasmid kits used for minipreps and QIAquick PCR purification kits were purchased from Quiagen Ltd and used according to the manufacturers' instructions. DNA sequencing was performed using Prism cycle sequencing reagents from Perkin Elmer Ltd and an ABI 373 automatic sequencer. RT-PCR was carried out using an Access RT-PCR System kit purchased from Promega UK according to the manufacturer's instructions. PCR products were cloned using a pGEM-T Vector kit purchased from Promega UK and used according to the supplied instructions.

Degenerate synthetic oligonucleotides were designed and synthesized based on the sense (S) and antisense (A) reverse translations of the three sequences isolated after proteolytic digestion of purified 13-HPOL (see Example 2). The degenerate oligonucleotides were used (1) to determine the arrangement of these three peptides in the primary structure of the enzyme and (2) to generate DNA fragments corresponding to the sequences between the peptides.

Isolation of Genomic DNA

Frozen leaf material (5 g) was crushed into a powder in liquid nitrogen in a pre-cooled pestle and mortar. The nitrogen was allowed to evaporate and the powder transferred to a Dounce homogenizer containing CTAB buffer (200 mM Tris-Cl pH 8.0, 20 mM EDTA, 1.4 M NaCl, 2% hexadecyltrimethylammonium bromide (CTAB) (w/v), 1% PVP 40,000 (w/v), 28 mM 2-mercaptoethanol v/v, 20 ml). Several strokes of the homogenizer were required to homogenize the powder. The homogenate was transferred to a Falcon tube (50 ml) and incubated at 65° C. for 90 min. Chloroform: isoamyl alcohol (10 ml, 24:1 v/v) was added and mixed in. The mixture was centrifuged at 3,000 g for 60 min which resulted in 3 layers. The upper aqueous layer was transferred to a fresh tube and an equal volume of isopropanol added and gently mixed. Following centrifugation at 3,000 g for 20 min, the supernatant was discarded. The pellet was washed with ethanol: 200 mM ammonium acetate (7:3, v/v, 25 ml) and centrifuged as before. The final pellet was resuspended in TE buffer (10 mM Tris-Cl pH 7.5, 1 mM EDTA, 0.5 ml) by heating at 65° C. RNase was added to a final concentration of 600 ng/ml and the solution incubated at 37° C. for 1 hr. The yield and purity were determined spectroscopically and by agarose gel electrophoresis.

Isolation of Total RNA from Guava Fruit

Plant material (1 g) was crushed to a fine powder in liquid nitrogen in a pre-cooled pestle and mortar. The nitrogen was allowed to evaporate and the powder transferred to a Dounce homogenizer. Lysis buffer (200 mM Borax, 30 mM EGTA, 10 mM DTT, 1% w/v SDS, 1% w/v sodium deoxycholate, 2% PVP 40,000, 0.5% v/v NP-40, 5 ml at 80° C.) was added and the powder homogenized. The homogenate was transferred to a Universal flask (30 ml), and proteinase K (125 μl @ 20 mg/ml) added. This mixture was incubated at 42° C. for 90 min with shaking sufficient to mix the contents without excessive foaming. Aliquots of the mixture (1 ml) were transferred to microcentrifuge tubes (1.5 ml) and a solution of KCl (1 M, 190 μl) added. After mixing, the tubes were incubated on ice for 1 h and then centrifuged for 10 min. Aliquots (0.5 ml) were transferred to fresh microcentrifuge tubes and LiCl (4 M, 0.5 ml) added. Following mixing, the tubes were incubated at 4° C. overnight. After centrifugation for 10 min, the supernatant was discarded. The pellets were washed with LiCl (2 M, 200 μl) and centrifuged as before. The supernatant was discarded and the pellets resuspended in TE buffer (200 μl). The samples were pooled and the RNA (970 μg) quantified by UV spectrophotometry.

Purification of Messenger RNA (mRNA) from Total RNA mRNA (18.8 μg, 1.9% yield) was purified from the total RNA by using an mRNA purification kit (Pharmacia Biotech) as described by the manufacturer. The kit uses spun columns of oligo(dT)-cellulose that bind the polyadenylated RNA (mRNA) by affinity interaction.

Construction and Screening of a cDNA Library from Immature Guava Fruit

Construction of the cDNA library was carried out using the ZAP-cDNA Gigapack II Gold Cloning Kit from Stratagene Ltd. following the provided protocols. Accordingly, a sample of total RNA (831 μg) was prepared from immature guava fruits (2 g) as described above. The mRNA (8.6 μg) was isolated (see above) from the majority of this material (670 μg). The yield (1.2%) is in agreement with those from other eukaryotic sources. Five ng of this mRNA was used to construct a cDNA library in the directional vector λZAP (Stratagene, Cambridge). The original library of 7.3×10 clones was amplified to give a stable stock of phage at ~5×10 plaque forming units/ml (pfu/ml).

Polymerase Chain Reaction (PCR)

Several sets of conditions were used to perform PCR depending on the template and oligonucleotides used as well as the number of cycles and the temperatures of the various steps. The reaction conditions were the same in all cases with the only variations being in template concentration, oligonucleotide concentration, number of cycles, temperatures used in each cycle and total volume of the reaction. The conditions used were: 50 mM KCl, 10 mM Tris-Cl pH 9.0 (at 25° C.), 0.1% Triton X-100 (v/v), 1 mM MgCl$_2$, 200 μM dNTP's, 25 U/ml Taq DNA polymerase.

The following cycle parameters and template and oligonucleotide concentrations for the various PCRs were as follows: genomic DNA with degenerate oligonucleotides (0.5 μg template; 1 nmole oligonucleotide; 60 cycles of start at 94° C. for 1 min duration, of annealing at 45° C. for 1 min, of elongation at 72° C. for 1 min); pGEM13-15 with degenerate oligonucleotides (2 μl miniprep DNA template; 0.4 nmoles oligonucleotide concentration; 20 cycles of start at 94° C. for 1 min, of annealing at 45° C. for 0.5 min, of elongation at 72° C. for 0.5 min); genomic/pGEM13-15 with Guv13&Guv15a (0.5 μg or 1 μl miniprep DNA template; 1 nmole oligonucleotide; 30 cycles of start at 94° C. for 1 min, of annealing at 50° C. for 1 min, of elongation at 72° C. for 1 min). Conditions similar to those used for genomic/pGEM13-15 with Guv13&Guv15a were used for the following except as specifically noted: RACE PCRs (either 1 µl of λ DNA or 5 µl of λ phage supernatant with 30 and 60 cycles, respectively, and with 0.01 nmoles of oligonucleotide); screening RACE clones (1 µl miniprep DNA, 0.05 nmoles oligonucleotide, and 10 cycles); nested PCRs (5 µl cleaned PCR as template, 0.1 nmoles oligonucleotide, annealing temperature of 54° C., and 20 cycles); screening PCR (1 µl miniprep DNA, 0.1 or 0.05 nmoles oligonucleotide, annealing temperature of 54° C. for 10 cycles); PCRs with the second set of degenerate oligonucleotides (0.5 µg genomic DNA or 5 µl λ phage supernatant, 0.25 oligonucleotide concentration, and 60 cycles). In control reactions, either oligonucleotides or template were omitted, but the corresponding volume of water was added.

Results

PCR was performed using single oligonucleotides or six pairs of oligonucleotides both with and without genomic DNA as template. The pairs of oligonucleotides were termed 12S&13A, 12S&15A, 13S&15A, 13S&12A, 15S&12A and 15S&13A. For each of the 6 possible arrangements of the peptides in the primary structure of the enzyme, one would expect a different set of PCR products from the reactions. For example, if the arrangement of the peptides was 12-13-15 then the 12S&13A, 12S&15A and 13S&15A PCRs would give products with the 12S&15A product being almost the same size as the other two products added together. After some degree of optimization, products were visible in these reactions and unique products could be observed on a 2% agarose gel of these reaction products.

The agarose gel showed only 2 unique bands, in the 13S&12A and 13S&15A lanes. The 13S&15A product was bigger than the 13S&12A product. This suggested that the orientation of the peptides was 13-12-15. From this, it was expected that a unique product would be observable in the 12S&15A reaction. The product observed was smaller than either of the other two unique products, suggesting that the arrangement of the peptides was 13-12-15, with 12 and 15 being very close together. Calculating the sizes of the PCR products from their mobility on an agarose gel gave the following sizes:13S&15A, ~160 bp; 13S&12A, ~140 bp; and 12S&15A, ~50 bp. The size of the unique products indicated that the sequence data would not be a major part of the gene sequence.

The 13S&15A unique product was purified from an agarose gel and used in a ligation with pGEM-T (Promega, Southampton), a vector designed for the efficient cloning of PCR fragments by the T-tail method (See Promega technical Bulletin TB 150). Two clones were picked and used as template in PCRs with 13S&12A, these clones produced products with the same size as the 13S&12A product observed with the genomic DNA template. This confirmed that the cloned 13S&15A fragments did contain the DNA sequence of peptide 12. The resulting plasmid was named pGEM13-15. Plasmid DNA was sequenced and the amino acid sequence derived (codons 151 to 204 in FIG. 2).

This sequence confirmed the following assumptions: (1) the three peptides were from the same peptide chain; (2) the cloned DNA fragment was part of the gene encoding these peptides since the coding sequences for all three were present as part of an open reading frame; and (3) the peptides were very close within the primary structure of the enzyme. Each peptide was cleaved at a lysine residue, as expected from the use of trypsin during the proteolytic digestion of the purified lyase. See Example 2.

A search of the SWISS-PROT and PATTCHX protein databases with the amino acid sequence from this fragment failed to show any protein with a high level of similarity. The degree of dissimilarity between the guava derived sequence and allene oxide synthases suggested that the cloned sequence did not come from a guava allene oxide synthase but from the desired lyase gene. The cloned sequence allowed the design of oligonucleotides that were specific for the lyase gene. The sequences chosen were from within the determined sequence rather than from the ends since the ends were derived from the degenerate oligonucleotides and thus did not necessarily represent the actual guava DNA sequence.

Example 4

Molecular Cloning of the Gene Encoding Guava 13-HPOL

Results

Reverse Transcriptase Polymerase Chain Reaction (RT-PCR)

First strand cDNA was synthesized from either total or poly(A)+RNA using an oligo-d(T)-adaptor (Table 3, summarizing reaction conditions). The first strand cDNA was then used directly in PCR reactions without purification (Table 4, summarizing reaction conditions). The reaction conditions were the same in all cases except for the amount of template used and DNA polymerase (either AmpliTaq DNA polymerase (Perkin Elmer) or Expand High Fidelity (Boehringer Mannheim)).

TABLE 3

| Reaction Conditions Used for Reverse Transcriptase (1 hour at 30° C.) | |
|---|---|
| Component | Amount Used |
| Total RNA form immature fruit or mRNA pre-treated at 65° C. for 5 min | 5 µg |
| | 1 µg |
| Oligo-dT adaptor ($^5$'ATG AAT TCG GTA CCC GGG ATC CTT TTT TTT TTT TTT TTT$^{3'}$) | 80 pmoles |
| 5 × first strand buffer | 10 µl |
| DTT | 1 mM |
| dNTP | 1 mM for each |
| RNAsin | 50 units |
| M-MLV-RT | 400 units |
| Water | to 50 µl |

TABLE 4

Reaction Conditions Used for PCR

| Component | Amount Used |
|---|---|
| guava cDNA (added at 80° C.) | 20–100 ng |
| dNTP | 200 μM for each |
| KCl | 50 mM |
| MgCl2 | 3 mM |
| Tris-HCl | 10 mM, pH 8.3 |
| upstream primer | 20 pmoles |
| downstream primer | 20 pmoles |
| Taq polymerase | 1.25 units |
| Water | to 50 μl |
| Reaction cycle parameters | –94° C., 2 min; 1 cycle |
| | –57 to 62° C., 1 min; 72° C., 1 min; |
| | 94° C., 1 min; 30 cycles |
| | –72° C., 10 min; 1 cycle |

Synthesis of Lyase Specific Oligonucleotide Primers

Specific oligonucleotide sequences corresponding to sections of the nucleotide sequence of the partial guava clone described in Example 3 were synthesized using methods known in the art (Sambrook et al., 1989).

5' Rapid Amplification of cDNA Ends (5' RACE)

Specific RNA sequences from mRNA (1 μg) were converted into first strand cDNA using a 5' RACE system (GibcoBRL) as described by the manufacturer.

Cloning and Sequencing of the 3' End of the Transcript Using 3' RACE

The 3' RACE (Rapid Amplification of cDNA Ends) method utilizes a gene-specific upstream primer for PCR, and a downstream primer based on the "adaptor sequence" at the 5' end of the primer used in the reverse transcriptase-catalyzed synthesis of the cDNA. The cDNA was prepared using total guava RNA (5 μg) and a gene-specific primer.

3' RACE reactions were carried out at an annealing temperature of 57° C. The first round PCR was primed with guava cDNA (1 μl, corresponding to an original 0.1 μg of total RNA). A gene-specific upstream primer was used with an oligo-adaptor downstream primer. The oligo-dT anneals to the poly-A tail of the mRNAs and the "adaptor" part is another 20 bases of known sequence tagged on the 5' tail of the primer. This sequence was later used as downstream primer for 3' RACE, while the upstream primer was based on the sequence identified in Example 3. No band was obtained when the reaction products were run an agarose gel.

A second round PCR reaction was primed with the first round reaction products (0.1 μl) and a gene-specific primer as a nested upstream primer (a nested primer is one that corresponds to a sequence within those used in the first round). The downstream primer was either the oligo-adaptor or one of two gene-specific primers, termed A7205 or A7206, the latter two being complementary to the sequence of the putative 3' UTR (UnTRanslated sequence) obtained as in Example 3.

A third round PCR reaction was primed with the second round product (0.1 μl, amplified with A7099 and the oligo-adaptor as primer). A third gene-specific nested upstream primer (A7203) and the oligo-adaptor were used as primers.

Cloning and Sequencing of the 5' End of the Transcript Using 5' RACE

Given that the cloning of the 3' end of the transcript required three rounds of PCR and that there was an appreciable amount of contamination of the total RNA preparation with putative genomic DNA, fresh RNA was prepared and then a poly-A+ selection was performed prior to cDNA synthesis for 5' RACE. The hot borate extraction procedure (Wan and Wilkins, 1994) was used to recover total RNA. This proved far superior to the standard method based on guanidinium thiocyanate and phenol-chloroform (Chomczynski and Sacchi, 1987). Poly-A+ selection was carried out as described above.

The cDNA synthesis for 5' RACE was accomplished using a kit (GibcoBRL) as described by the manufacturer. This technique facilitates the isolation and characterization of 5' ends from low-copy messages as it utilizes a gene-specific primer for first strand cDNA synthesis.

First strand cDNA synthesis was primed using the lyase gene-specific antisense oligonucleotide A7204. This permitted cDNA conversion of the mRNA (1 μg) from immature guava fruits. The first strand cDNA product was purified and then reacted with a terminal deoxynucleotide transferase enzyme (TdT, GibcoBRL) to add homopolymeric dC tails to the 3' ends of the first strand cDNA.

The tailed cDNA was then amplified by PCR using another lyase-specific oligonucleotide and an anchor primer that allowed amplification from the homopolymeric tail. The annealing temperature used in these PCR reactions was 60° C.

Cloning and Sequencing of the Full-length cDNA

Gene-specific primers were synthesized to correspond to the putative start of the coding sequence (two different methionines were selected) and at the stop codon. A Kozak consensus sequence for translation initiation was included in the upstream primer (Kozak, 1989). In addition to this, the restriction sites BamHI and EcoRI were incorporated at the 5' and 3' ends respectively for future sub-cloning work.

The primers for this work were ordered with the DMT (dimethoxy-trityl) protecting groups still in place. They were purified by HPLC (Brash et al., 1996), then deprotected and quantified by UV spectroscopy prior to use in PCR.

The PCR reaction was primed with guava cDNA prepared from guava mRNA (1 μg) and the lyase-specific primers in the following combinations 1) B6966 with B6967 and 2) C1914 with B6967. The annealing temperature used was 60° C. For these PCR reactions, a special DNA polymerase mixture with proof-reading capabilities was used (Expand High Fidelity, Boehringer Mannheim).

Both PCR reactions, i.e., using the two different upstream primers, gave a band of the expected size (1.5 kb). The two different products were subcloned into the pCR2.1 vector (Invitrogen) and sequenced.

Results

Cloning and Sequencing of the 3' End of the Transcript Using 3' RACE

The second round PCR reaction gave a unique band with the primer A7205 (250 bp) and also a unique band (220 bp) with A7206. The difference in size of these two PCR products (30 bp) matches the expected distance between the two downstream primers A7205 and A7206. Furthermore, the sizes of 220 and 250 bp were exactly what was expected by direct cloning of the DNA fragment derived in Example 3.

The 220 or 250 bp product was, however, too short to encode the fall length of the remaining 3' coding sequence and 3' UTR of the lyase. The expected size of the correct PCR product was at least 950 bp, and it could have significantly longer depending on the length of the 3' UTR. This finding was interpreted as indicating that the original clone was derived from a fragment of genomic DNA that had been cloned into the cDNA library. The coding sequence obtained corresponded to an exon, and this led into an intron (non-coding sequence, originally suspected to be 3'UTR) immediately after the coding sequence for Asn-Ile-Gly.

During the same series of second round PCR reactions, the reaction using the oligo-adaptor downstream primer amplified 2 products (450 and 1,100 bp). The larger product is compatible in size to the expected product from the 3' end of the lyase cDNA.

During the third round PCR reaction, a 1,000 bp product corresponding to the expected size was obtained. This PCR product differed in size from the second round product by 100 bp, which corresponds well to the different positions of the nested upstream primers in these two PCR reactions. This 1,000 bp product was sub-cloned into the pCR2.1 vector (Invitrogen) and sequenced.

The sequence showed that the PCR product contained the sequence identified in Example 3 together with the remainder of the 3' coding sequence plus 186 bp of 3' UTR.

Cloning and Sequencing of the 5' End of the Transcript Using 5' RACE

Primer C1589 gave a unique band of the expected size (500 bp) as did primer C1588 (700 bp). The 700 bp PCR product was sub-cloned into the pCR2.1 vector (Invitrogen) and sequenced.

Cloning and Sequencing of the Full-length cDNA

Figure 2A:
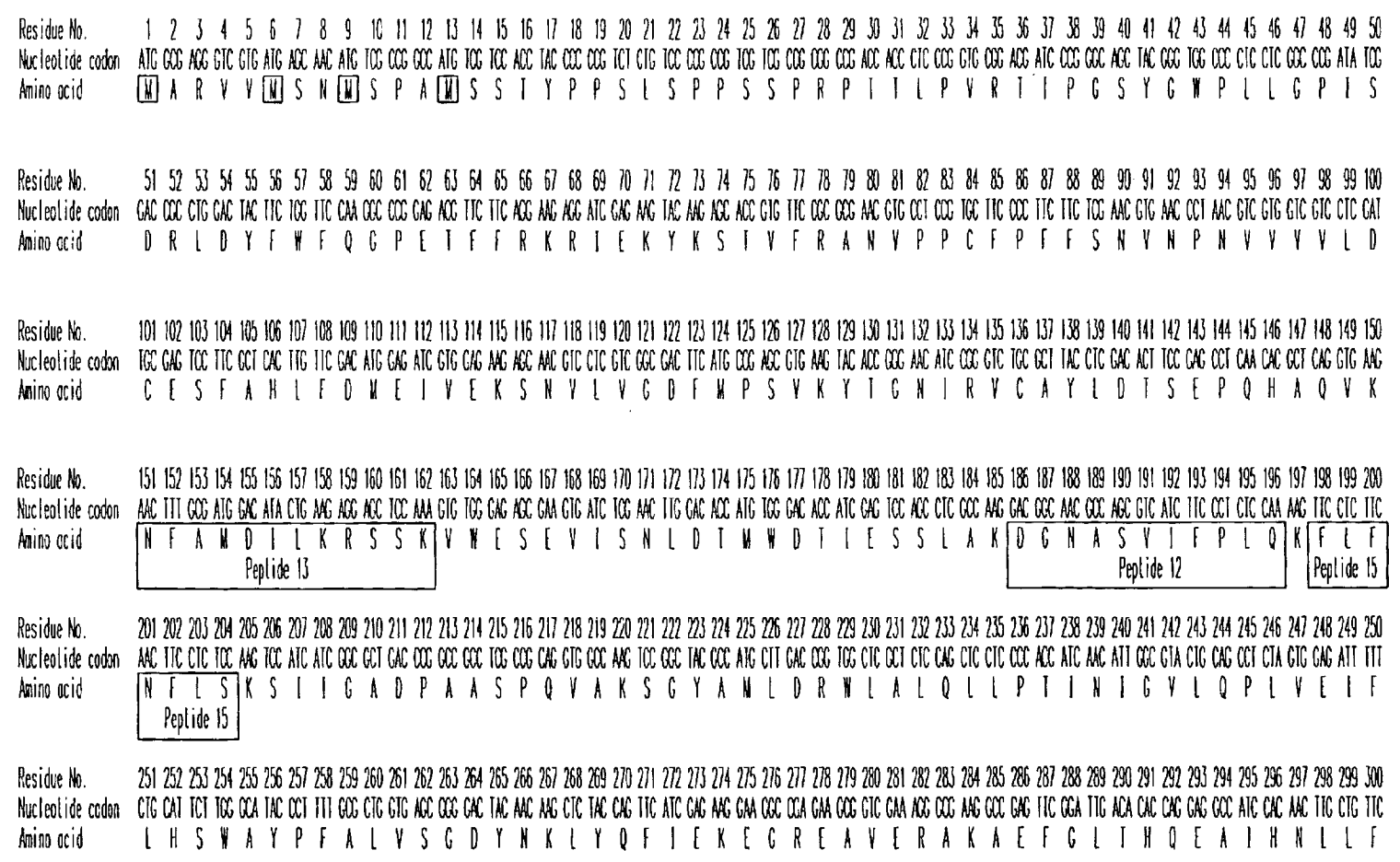

The complete sequence of the product of the PCR reactions is shown in FIG. 2. The translated sequence encodes a total of 488 amino acids corresponding to a protein with a calculated molecular weight of 54,817 Daltons, a molar extinction coefficient (at 280 nm) of 63,590±5%, and an isoelectric point of 7.29.

Example 5

Expression of the Gene Encoding Guava 13-HPOL

Bacterial Transformation

The full-length cDNA clone of 13-HPOL (See FIG. 2) was inserted into the *Escherischia coli* expression plasmid pET30b (Novagen). The pET30b system contains a sequence that "tags" the expressed protein with a number of histidine residues. This provides a means of purifying the protein by affinity chromatography using a nickel ligand.

Accordingly, the pET30b plasmids and the pCR2.1 clone containing the 13-HPOL cDNA were linearized with 2 different restriction enzymes (BamHI and HindIII) and then ligated together. The pET30b:13-HPOL constructs were used to transform *E. coli* strain BL21 (Novagen).

Expression of 13-HPOL in Transformed *E. coli* Cells

The transformed BL21 cells were cultured overnight at 37° C. and 280 rpm in LB medium (3 ml, prepared by dissolving tryptone (10 g), yeast extract (5 g), and NaCl (10 g) in 1 liter of water, adjusting the pH to 7.0 and autoclaving). The antibiotic kanamycin (30 mg) was added aseptically after autoclaving. A portion of the resulting culture (0.2 ml) was then transferred to Terrific Broth (TB, 10 ml, prepared by dissolving bacto-tryptone (12 g), bacto-yeast extract (12 g), and glycerol (4 ml) in deionized water (900 ml), autoclaving and then adding a sterile solution (100 ml) containing 50 μg/ml kanamycin, 0.17 M $KH_2PO_4$, and 0.72 M $K_2HPO_4$) and allowed to grow until the optical density at 260 nm ($OD^{260}$) reached 0.6. This culture was used to inoculate 50 ml of TB containing 50 μg/ml of kanamycin, which was then placed at 28° C. and 200 rpm and a heme precursor, δ-aminolevulimic acid (1 mM), was added followed by the inducer IPTG (0.4 mM) one hour later. The induced cultures were left for a further period of time (4 or 16 hours) and the cells harvested by centrifugation (5,000 rpm for 7 min at 4° C.). The precipitated cells were washed by resuspending them in Tris-HCl buffer (50 mM, pH 7.9) followed by recentrifugation as before.

The resulting pellet of cells was resuspended in Tris-acetate buffer (0.1 M, pH 7.6) containing sucrose (0.5 M), EDTA (0.5 mM) and lysozyme (1 mg/ml). After 30 min on ice, the mixture was centrifuged as before to obtain a pellet of spheroplastes. These were resuspended in potassium phosphate buffer (0.1 M, pH 7.6) containing magnesium acetate (6 mM), glycerol (20% v/v) and DTT (0.1 mM) and the mixture left for 10 min at −80° C. Following this, a protease inhibitor was added (PMSF, 1 mM) and the cells sonicated (2×30 seconds). 13-HPOL activity was readily detected in this sonicate using the methods described herein.

SDS-PAGE Analysis of 13-HPOL Expression

Proteins from the transformed and induced cells were compared by SDS-PAGE with those from control cultures. The results from the analysis of the pET30b: 13-HPOL constructs in *E. coli* strain BL21 clearly showed that a huge amount of protein with the expected molecular weight (54 kD) had been made.

Example 6

Expression of Variants of the Gene Encoding Guava 13-HPOL Under Varied Conditions Four different cDNA clones of 13-HPOL (13-HPOL-Met1, -Met6, -Met9, -Met13) were inserted into the *E. coli* expression plasmid pET30b. The pET30b:13-HPOL were used to transform *E. coli* strain BL21 (Novagen) under various conditions.

Methods

Bacterial Strain and Plasmid

The bacterial host strain BL21(DE3): (F-ompT hsdSB (RB-mB-) gal dcm (DE3)) and pET30b plasmids were obtained from Novagen.

Constructs

Four expression plasmids (pET30b:13HPOL-Met1, -Met6, -Met9 and -Met13) were made according to procedures well known in the art (e.g., Sambrook et al., 1989). Construct pET30b:13HPOL-Met1 was made as follows: cDNA encoding the 13-HPOL-Met1 in pCR2.1 was cut with BamHI and HindIII and subcloned into the expression vector plasmid pET30b (digested also with BamHI and HindIII). The 13-HPOL-Met1 construct was used to transform *E. coli* strain XL1-Blue by heat shock. Colonies obtained after transformation were grown in 2 ml of LB medium containing 30 μg/ml of kanamycin at 37° C. overnight and plasmid DNAs were purified using a Qiagen Plasmid Kit. The purified DNA was cut with BamHI and HindIII to screen for the correct plasmid DNA, pET30:13-HPOL-Met1. Then, the plasmid DNA was used for transformation of *E. coli* strain BL21(DE3) to express the 13-HPOL.

Constructs pET30b:13-HPOL-Met6, -Met9, -Met13 were made using the construct pET30b:13-HPOL-Met1. PCR products of approximately 680 to 700 bp of Met6, Met9, and Met13 with BamHI and MscI cleavage sites were each subcloned into pCR2.1 and subsequently digested with BamHI MscI. The pET30 digestion product of pET30:13-HPOL-Met1 and the PCR digestion product of the preceding step were purified and ligated to form Constructs pET30b:13-HPOL-Met6, -Met9, -Met13.

A PCR reaction was carried out under the following conditions: 20–100 ng of cDNA, 1 μl dNTP 10 mM, 5 μl PCR buffer (10×) with 15 mM $MgCl_2$, 5 μl of 4 μM primer downstream, 0.75 Expand™ High Fidelity, Boehringer Mannheim, and water up to 50 μl. The PCR buffer (10×; Expand™ High Fidelity) consisted of 20 mM Tris-HCl (pH7.5), 100 mM KCl, 1 mM DTT (dithiothreitol), 0.1 mM EDTA, 0.5% (v/v) Tween 20, 0.5% (v/v) Nonidet P40, and 50% (v/v) glycerol. The reaction was primed with the cDNA encoding the 13-HPOL-Met1 in pCR2.1 and using as primer either (1) Guava-up-Met6 (5'GCG GAT CCG GCC ATG AGC AAC ATG TCG3') (SEQ ID NO:16) and Guava-down (5'AAT GTT GAT GGT GGG GAG GAG3') (SEQ ID NO:17), (2) Guava-up-Met9 (5'GCG GAT CCG GCC ATG TCG CCG GCC AT3') (SEQ ID NO:18) and Guava-down, or (3)Guava-up-Met13 (5'GCG GAT CCG GCC ATG TCG TCC ACC TAC3') (SEQ ID NO:19).

In each PCR reaction, a unique band was amplified which corresponded to the first 680–700 bp of the 13-HPOL starting from methionine in position 6, 9, or 13. After purification (QIAEX II gel extraction kit), each DNA fragment was subcloned into the vector pCR2.1 and sequenced.

Preparation of Bacterial Cultures

The bacterial cultures were prepared according to the method of Hoffman et al. (1995). Specifically, a single bacterial colony from a complex agar plate containing 30 μg/ml of kanamycin was grown in 1 ml of LB medium containing 50 μg/ml of kanamycin for 3 hours at 37° C. A small aliquot (200 μl) of this culture was then used to inoculate 10 ml of LB or TB containing 50 μg/ml of kanamycin and the culture was again grown at 37° C. After 3 hours, this culture was used to inoculate 50 ml of LB or TB medium containing 30 μg/ml of kanamycin and with or without 1 mM of δ-aminolevulinic acid (δ-ALA).

The culture was grown at 15° C., room temperature (23° C.) or 28° C. After 1 hour, the inducer isopropyl-β-D-thiogalactopyranoside (IPTG, 0.4 mM) was added or not. The culture was grown 4 hours, 24 hours or 48 hours at 15° C., room temperature (23° C.) or 28° C.

The bacterial cells were centrifuged at 4° C. for 10 min (5,000 rpm). The precipitated cells were washed by resuspension in 10 ml of Tris-HCl buffer 50 mM pH7.9 and were centrifuged as before. Sonicates were prepared as described in Example 5.

The activity of the 13-HPOL expressed in the BL21 cells was measured using the spectrophotometric assay and by HPLC as described above. The sample was diluted 10-fold, and 5 or 10 μl aliquots were assayed using 4–5 mg of 13(S)-hydroperoxylinolenic acid in 0.5 ml of potassium phosphate pH 7.4. The decrease in absorbance at 235 nm was immediately recorded. The activity was verified using GC-MS of the volatile C-6 product as described above. No activity could be detected in the negative control, which consisted of the sonicated protein preparation obtained from the BL21 cells transformed with pET30 only.

Results

The results are shown in Table 5. At 15° C., no lyase activity was detectable. The activity at 23° C. was higher than at 28° C. Activities were highest after 48 hours of culture. The best activities were obtained without δ-ALA and without IPTG. Thus, in the system used here, with the pET30 plasmid and its T7 RNA polymerase promoter, and with the cells grown in a rich medium (TB), addition of heme precursor or IPTG inducer does not help with expression of active lyase.

TABLE 5

Activity of 13-HPOL-Met1 after expression in E. coli cells in different conditions of culture

| | Activity (OD. min$^{-1}$) | | | | | |
|---|---|---|---|---|---|---|
| | 4 hours | | 24 hours | | 48 hours | |
| | 23° C. | 28° C. | 23° C. | 28° C. | 23° C. | 28° C. |
| +δ-ALA −IPTG | 0.55 | 0.32 | 1.9 | 1.01 | 2.35 | 1.13 |
| −δ-ALA −IPTG | 0.7 | 0.45 | 2.34 | 1.44 | 3.01 | 2.6 |
| +δ-ALA +IPTG | — | 0.27 | — | 0.4 | — | — |
| −δ-ALA +IPTG | — | 0.14 | — | 0.24 | — | — |

Proteins from the transformed and induced cells were compared by SDS-PAGE. A very high amount of protein (accounting for more that half of the total cellular protein) with the expected molecular weight was expressed under all the different conditions of culture. Relatively lower amounts of protein, but the highest lyase activity, were obtained when the cells were grown without δ-ALA and IPTG. This may reflect the fact that there is a very high basal induction in this system. Including a further stimulus for protein expression resulted in even lower recovery of correctly folded protein with catalytic activity. In fact, when the cells are examined under the microscope, many inclusion bodies were seen. The number of inclusion bodies was highest in cells grown with IPTG, in agreement with the concept that the bacteria cannot handle this level of expressed protein.

Substrate specificity of the expressed pET30:13-HPOL-Met1 was examined by incubating an aliquot of sonicated preparation with the following substrates: 13(S)-hydroperoxylinoleic acid; 9(S)-hydroperoxylinoleic acid; 13(S)-hydroperoxylinolenic acid; 15(S)-HPETE, which is the 15-hydroperoxide of arachidonic acid. The results showed that the metabolism of the 9(S)-hydroperoxylinoleic acid and 15(S)-HPETE by the 13-HPOL-Met1 is low in comparison to the rate of reaction with 13(S)-hydroperoxylinolenic acid. In addition, the 13-HPOL-Met1 is at least 10-times more active with 13-(S)-hydroperoxylinolenic acid as the substrate compared to 13-hydroperoxylinoleic acid.

The expressions of pET30:13-HPOL-Met1,-Met6,-Met9 and -Met13 were also compared. To compare the activities of the four pET30:13-HPOL constructs, the plasmids were expressed under identical conditions. Each was assessed for lyase activity (UV assay) and the level of protein expression (SDS-PAGE). The results from two independent experiments showed that these 4 different enzyme constructs were expressed at similar levels. All four constructs gave active lyase, although with a three-fold range of activities. The Met9 and Met13 gave the highest activities, 0.90 and 0.92 OD.min$^{-1}$, respectively. Met6 activity was 0.60 OD.min$^{-1}$. Met1 activity was lowest at 0.30 OD.min$^{-1}$.

Example 7

Cleavage of 13-HPOD to Hexanal Using Recombinant Guava 13-HPOL

Methods

A solution of 13-HPOD (55 g/l) was made as described in U.S. Pat. No. 5,464,761 and diluted 10 fold with buffer (0.1M potassium phosphate, pH 8.5). Three different quantities of recombinant 13-HPOL were added to the diluted 13-HPOD solution in order to analyze the amount of 13-HPOD cleavage by the recombinant protein. Thus, either 0, 10, or 25 µl of the 13-HPOL containing bacterial lysate (see Example 5) were added to 2 ml of the diluted 13-HPOD solution, which contained 11 mg of 13-HPOD. In samples without bacterial lysate, the lysate was replaced with 10 µl of distilled water. The samples were stirred for 30 min at room temperature (20° C.). Each sample was then extracted once with 2 ml of diethylether containing 137 mg/l n-hexanol as an internal standard. Subsequently, 1 µl of the organic extract was injected onto a 15 M SPwax gas chromatography column using the following temperature program: 50° C. for 2 min and ramp to 160° C. at 5° C. each minute. The amount of hexanal formed was calculated by comparison of the hexanal peak area to that of the internal standard.

Results

The amount of hexanal in the control samples, which contained no 13-HPOL containing bacterial lysate, was 61 mg/l. The hexanal in the control samples was formed by the soy flour used in the preparation of the 13-HPOD substrate. Thus, 61 mg/l was subtracted from the total amount of hexanal in the samples to determine the amount of hexanal formed by the recombinant 13-HPOL in the bacterial lysate. The amount of hexanal formed by the recombinant 13-HPOL in 10 µl of bacterial lysate was 140 µg. By extrapolation, one liter of lysate would produce 14 grams of hexanal.

Throughout this application, various publications are referenced. The disclosures of these publications in their entireties are hereby incorporated by reference into this application in order to more fully describe the state of the art to which this invention pertains.

Although the present process has been described with reference to specific details of certain embodiments thereof, it is not intended that such details should be regarded as limitations upon the scope of the invention except as and to the extent that they are included in the accompanying claims. Thus, the preceding examples are intended to illustrate, but not limit, the invention. While they are typical of those that might be used, other procedures known to those skilled in the art may be alternatively employed.

REFERENCES

1. Bradford M. M. (1976). A rapid and sensitive method for the quantitation of microgram quantities of protein utilizing the principle of protein-dye binding. *Anal. Biochem.* 72:248–254.
2. Brash, A. R., Boeglin, W. E. Chang, M. S. and Shieh, B. H. (1996). Purification and Molecular cloning of an 8R-Lipoxygenase from the Coral *Plexaura homomalla* Reveal the Related Primary Structures of R- and S-Lipoxygenases. *J. Biol. Chem.*, 271:34:20949–20957.
3. Chomczynski, P. and Sacchi, N. (1987). Single Step Method of RNA Isolation by Acid Guanidinium Thiocyanate-Phenol-Chloroform Extraction. *Anal Biochem.* 162, 156–159.
4. Dayhoff, et al., *Atlas of protein Sequence and Structure.* Nat'l. Biomed. Res. Found., Washington, D.C. (1978)
5. Fauconnier, M. L., Perez, A. G., Sanz, C., Marlier, M. (1997). Purification and Characterization of Tomato Leaf (*Lycopersicon esculentum* Mill.) Hydroperoxide Lyase. *J. Agric. Food Chem.* 45:4232.
6. Hatanaka A. (1993). The biogeneration of green odour by green leaves. *Phytochemistry* 34:1201–1218.
7. Hatanaka A., Kajiwara, T. and Sekija, J. (1987). Biosynthetic pathway for C6—aldehydes formation from linolenic acid in green leaves. *Chemistry and Physics of Lipids* 44:431–361.
8. Hess D., Covey T. C., Winz R., Brownsey R. W. and Aebersold R. (1993). Analytical and micro preparative peptide mapping by high performance liquid chromatography/electrospray mass spectrometry of proteins purified by gel electrophoresis. *Protein Science* 2:1342–1351.
9. Hoffman, et al., (1995) *Protein Expression and Purification* 6:646–654.
10. Kozak, M. (1989). The Scanning Model for Translation: An update. *J. Cell Biol.* 108:229–241.
11. Laemmli U.K. (1970). Cleavage of structural proteins during the assembly of the head of bacteriophage T4. *Nature* 227:680–685.
12. Matsui K., Shibata Y., Kajiwara, T. and Hatanaka A. (1989). Separation of 13- and 9-hydroperoxide lyase activities in cotyledons of cucumber seedlings. Z. *Naturforsch.* 44c:883–885.
13. Matsui K, Toyota H., Kajiwara T., Kakuno T. and Hatanaka A. (1991). Fatty acid hydroperoxide cleaving enzyme, hydroperoxide lyase, from tea leaves. *Phytochemistry* 30:2109–2113.
14. Matsui, K., Shibutani, M., Hase, T., and Kajiwara, T. (1996). Bell Pepper Fruit Fatty Acid Hydroperoxide Lyase is a Cytochrome P-450 (CYP74B). *FEBS Lett.* 394:21–24.
15. Olias J. M., Rios J. J., Valle M., Zamora R., Sanz L. C. and Axelrod B. (1990). Fatty add hydroperoxide lyase in germinating soybean seedlings. *J. Agric. Food Chem.* 38:624–630.
16. Sambrook, J., Fritsch, E. F. and Maniatias, T. Eds. (1989) Molecular Cloning. A Standard Laboratory Manual. 2nd Edition. Cold Spring Harbour Laboratory Press.
17. Schreier P. and Lorenz G. (1982). Separation, partial purification and characterization of a fatty acid hydroperoxide cleaving enzyme from apple and tomato fruits. Z. *Naturforsch.* 37c:165–173.
18. Shibata Y., Matsui K, Kajiwara T. and Hatanaka, A. (1995). Purification and properties of fatty acid hydroperoxide lyase from green bell pepper fruits. *Plant Cell Physiology* 36:147–156.
19. Song W.-C. and Brash A. R. (1991). Purification of an allene oxide synthase and identification of the enzyme as a cytochrome P 450. *Science* 253:781–784.
20. Song W.-C., Funk C. D. and Brash A. R. (1993). Molecular cloning of an allene oxide synthase: A cytochrome P-450 specialized for the metabolism of fatty acid hydroperoxides. *Proc. Natl. Acad. Sci. USA* 90:8519–8523.
21. Tressl, R. and Drawert, F. (1973). Biogenesis of banana volatiles. *J. Agric. Food Chem.* 21:560–565.
22. Vick B. A. (1991). A spectrophotometric assay for hydroperoxide lyase. *Lipids* 26:315–320.
23. Vick B. A. and Zimmerman D.C. (1976). Lipoxygenase and hydroperoxide lyase in germinating watermelon seedlings. *Plant Physiol.* 57:780–788.
24. Wan, C. Y., and Wilkins, T. A. (1994). A Modified Hot Borate Method Significantly Enhances the Yield of High-Quality RNA from Cotton (*Gossypium hirsutum* L.). *Anal. Biochem.* 223:7–12.

What is claimed is:

1. A method of cleaving a 13-hydroperoxide of linoleic or α-linolenic acid into a $C_6$- aldehyde and a $C_{12}$- oxocarboxylic acid comprising contacting the 13-hydroperoxide with a recombinant protein produced by a vector comprising a nucleic acid encoding a fatty acid 13-hydroperoxide lyase comprising the amino acid sequence set forth in SEQ ID NO:1, wherein said recombinant protein has fatty acid 13-hydroperoxide lyase activity and wherein the amino acid sequence of the recombinant protein is present in a fatty acid 13-hydroperoxide lyase isolated from *Psidium guajava*, thereby cleaving the 13-hydroperoxide.

2. A method of preparing n-hexanal, 3-(Z)-hexen-1-al, 2-(E)-hexen-1-al, or their corresponding alcohols from 13-hydroperoxy-octadeca-9,11-dienoic acid or 13 hydroperoxy-octadeca-9,11,15-trienoic acid, comprising
   (a) contacting the 13-hydroperoxy-octadeca-9,11-dienoic acid or the 13 hydroperoxy-octadeca-9,11,15-trienoic acid with a recombinant protein produced by a vector comprising a nucleic acid encoding a fatty acid 13-hydroperoxide lyase comprising the amino acid sequence set forth in SEQ ID NO:1, wherein said recombinant protein has fatty acid 13-hydroperoxide lyase activity and wherein the amino acid sequence of the recombinant protein is present in a fatty acid 13-hydroperoxide lyase isolated from *Psidium guajava*, thereby converting the 13-hydroperoxy-octadeca-9,11,-dienoic acid into n-hexanal or the 13 hydroperoxy-octadeca-9,11,15-trienoic acid into 3-(Z)-hexen-1-al; and either (b) recovering the n-hexanal or 3-(Z)-hexen-1-al;

(b') reducing the n-hexanal into n-hexanol or the 3-(Z) hexen-1-al into 3-(Z)-hexen-1-ol and recovering the hexanol or 3-(Z)-hexen-1-ol; or (b") isomerizing the 3-(Z)-hexen-1-al under temperature and pH conditions effective to obtain 2-(E)-hexen-1-al and either recovering the formed 2-(E)-hexen-1-al or reducing the 2-(E)-hexen-1-al to 2-(E)-hexen-1-ol and recovering the 2-(E)-hexen-1-ol from the medium.

3. A method of preparing a $C_6$- aldehyde, a $C_{12}$-oxocarboxylic acid, or their corresponding alcohols, from 13-hydroperoxy-octadeca-9,11-dienoic acid or 13 hydroperoxy-octadeca-9,11,15-trienoic acid, comprising (a) contacting the 13-hydroperoxy-octadeca-9,11-dienoic acid or the 13 hydroperoxy-octadeca-9,11,15-trienoic acid with a recombinant protein produced by a vector comprising a nucleic acid encoding a fatty acid 13-hydroperoxide lyase comprising the amino acid sequence set forth in SEQ ID NO:1, wherein said recombinant protein has fatty acid 13-hydroperoxide lyase activity and wherein the amino acid sequence of the recombinant protein is present in a fatty acid 13-hydroperoxide lyase isolated from *Psidium guajava*, thereby converting the 13-hydroperoxy-octadeca-9,11-dienoic acid into the $C_6$- aldahyde and the $C_{12}$-oxocarboxylic acid; and either (b) recovering the $C_6$-aldehyde or the $C_{12}$-oxocarboxylic acid;

(b') reducing the $C_6$-aldehyde or the $C_{12}$-oxocarboxylic acid to their corresponding alcohols and recovering the alcohols; or (b") isomerizing the $C_6$- aldehyde or the $C_{12}$-oxocarboxylic acid under temperature and pH conditions effective to obtain the isometic forms thereof and either recovering the isomeric forms or reducing the isomeric forms and recovering their corresponding alcohols from the medium.

4. A method of cleaving a 13-hydroperoxide of linoleic or α-linolenic acid into a $C_6$- aldehyde and a $C_{12}$-oxocarboxylic acid comprising contacting the 13-hydroperoxide with a recombinant protein produced by a vector comprising a nucleic acid encoding a fatty acid 13-hydroperoxide lyase comprising the amino acid sequence set forth in SEQ ID NO:2, thereby cleaving the 13-hydroperoxide.

5. A method of preparing n-hexanal, 3-(Z)-hexen-1-al 2-(E)-hexen-1-al, or their corresponding alcohols from 13-hydroperoxy-octadeca-9,11-dienoic acid or 13 hydroperoxy-octadeca-9,11,15-trienoic acid, comprising (a) contacting the 13-hydroperoxy-octadeca-9,11-dienoic acid or the 13 hydroperoxy-octadeca-9,11,15-trienoic acid with a recombinant protein produced by a vector comprising a nucleic acid encoding a fatty acid 13-hydroperoxide lyase comprising the amino acid sequence set forth in SEQ ID NO:2, thereby converting the 13-hydroperoxy-octadeca-9,11-dienoic acid into n-hexanal or the 13 hydroperoxy-octadeca-9,11,15-trienoic acid into 3-(Z)-hexen-1-al; and either (b) recovering the n-hexanal or 3-(Z)-hexen-1-al;

(b') reducing the n-hexanal into n-hexanol or the 3-(Z)-hexen-1-al into 3-(Z)hexen-1-ol and recovering the hexanol or 3-(Z)-hexen-1-ol; or (b") isomerizing the 3-(Z)-hexen-1-al under temperature and pH conditions effective to obtain 2-(E)-hexen-1-al and either recovering the formed 2-(E)-hexen-1-al or reducing the 2-(E)-hexen-1-al to 2-(E)-hexen-1-ol and recovering the 2-(E)-hexen-1-ol from the medium.

6. A method of preparing a $C_6$-aldehyde, a $C_{12}$-oxocarboxylic acid, or their corresponding alcohols, from 13-hydroperoxy-octadeca-9,11-dienoic acid or 13 hydroperoxy-octadeca-9,11,15-trienoic acid, comprising (a) contacting the 13-hydroperoxy-octadeca-9,11-dienoic acid or the 13 hydroperoxy-octadeca-9,11,15-trienoic acid with a recombinant protein produced by a vector comprising a nucleic acid encoding a fatty acid 13-hydroperoxide lyase comprising the amino acid sequence set forth in SEQ ID NO:2, thereby converting the 13-hydroperoxy-octadeca-9,11-dienoic acid into the $C_6$-aldehyde and the $C_{12}$-oxocarboxylic acid; and either (b) recovering the $C_6$-aldehyde or the $C_{12}$-oxocarboxylic acid;

(b') reducing the $C_6$-aldehyde or the $C_{12}$-oxocarboxylic acid to their corresponding alcohols and recovering the alcohols; or (b") isomerizing the $C_6$-aldehyde or the $C_{12}$-oxocarboxylic acid under temperature and pH conditions effective to obtain the isomeric forms thereof and either recovering the isomeric forms or reducing the isomeric forms and recovering their corresponding alcohols from the medium.

7. A method of cleaving a 13-hydroperoxide of linoleic or α-linolenic acid into a $C_6$-aldehyde and a $C_{12}$-oxocarboxylic acid comprising contacting the 13-hydroperoxide with a recombinant protein produced by a vector comprising a nucleic acid encoding a fatty acid 13-hydroperoxide lyase comprising the amino acid sequence set forth in SEQ ID NO:3, thereby cleaving the 13-hydroperoxide.

8. A method of preparing n-hexanal, 3-(Z)-hexen-1-al, 2-(E)-hexen-1-al, or their corresponding alcohols from 13-hydroperoxy-octadeca-9,11-dienoic acid or 13 hydroperoxy-octadeca-9,11,15-trienoic acid, comprising (a) contacting the 13-hydroperoxy-octadeca-9,11-dienoic acid or the 13 hydroperoxy-octadeca-9,11,15-trienoic acid with a recombinant protein produced by a vector comprising a nucleic acid encoding a fatty acid 13-hydroperoxide lyase comprising the amino acid sequence set forth in SEQ ID NO:3, thereby converting the 13-hydroperoxy-octadeca-9,11-dienoic acid into n-hexanal or the 13 hydroperoxy-octadeca-9,11,15-trienoic acid into 3-(Z)-hexen-1-al; and either (b) recovering the n-hexanal or 3-(Z)-hexen-1-al;

(b') reducing the n-hexanal into n-hexanol or the 3-(Z)-hexen-1-al into 3-(Z)-hexen-1-ol and recovering the hexanol or 3-(Z)-hexen-1-ol; or (b") isomerizing the 3-(Z)-hexen-1-al under temperature and pH conditions effective to obtain 2-(E)-hexen-1-al and either recovering the formed 2-(E)-hexen-1-al or reducing the 2-(E)-hexen-1-al to 2-(E)-hexen-1-ol and recovering the 2-(E)-hexen-1-ol from the medium.

9. A method of preparing a $C_6$- aldehyde, a $C_{12}$-oxocarboxylic acid, or their corresponding alcohols, from 13-hydroperoxy-octadeca-9,11-dienoic acid or 13 hydroperoxy-octadeca-9,11,15-trienoic acid, comprising (a) contacting the 13-hydroperoxy-octadeca-9,11-dienoic acid or the 13 hydroperoxy-octadeca-9,11,15-trienoic acid with a recombinant protein produced by a vector comprising a nucleic acid encoding a fatty acid 13-hydroperoxide lyase comprising the amino acid sequence set forth in SEQ ID NO:3, thereby converting the 13-hydroperoxy-octadeca-9,11-dienoic acid into the $C_6$- aldehyde and the $C_{12}$-oxocarboxylic acid; and either (b) recovering the $C_6$- aldehyde or the $C_{12}$-oxocarboxylic acid;

(b') reducing the $C_6$- aldehyde or the $C_{12}$-oxocarboxylic acid to their corresponding alcohols and recovering the alcohols; or (b") isomerizing the $C_6$- aldehyde or the $C_{12}$-oxocarboxylic acid under temperature and pH conditions effective to obtain the isomeric forms thereof and either recovering the isomeric forms or reducing the homeric forms and recovering their corresponding alcohols from the medium.

10. A method of cleaving a 13-hydroperoxide of linoleic or α-linolenic acid into a $C_6$-aldehyde and a $C_{12}$-oxocarboxylic acid comprising contacting the 13-hydroperoxide with a recombinant protein produced by a vector comprising a nucleic acid encoding a fatty acid 13-hydroperoxide lyase comprising the amino acid sequence set forth in SEQ ID NO:4, thereby cleaving the 13-hydroperoxide.

11. A method of preparing n-hexanal, 3-(Z)-hexen-1-al, 2-(E)-hexen-1-al, or their corresponding alcohols from 13-hydroperoxy-octadeca-9,11-dienoic acid or 13 hydroperoxy-octadeca-9, 11,15-trienoic acid, comprising (a) contacting the 13-hydroperoxy-octadeca-9,11-dienoic acid or the 13 hydroperoxy-octadeca-9,11,15-trienoic acid with a recombinant protein produced by a vector comprising a nucleic acid encoding a fatty acid 13-hydroperoxide lyase comprising the amino acid sequence set forth in SEQ ID NO:4, thereby converting the 13-hydroperoxy-octadeca-9,11-dienoic acid into n-hexanal or the 13 hydroperoxy-octadeca-9,11,15-trienoic acid into 3-(Z)-hexen-1-al; and either (b) recovering the n-hexanol or 3-(Z)-hexen-1-al;

(b') reducing to n-hexanol into n-hexanol or the 3(Z)-hexen-1-al into 3-(Z)-hexen-1-ol and recovering the hexanol or 3-(Z)-hexen-1-ol: or (b") isomerizing the 3-(Z)-hexen-1-al under temperature and pH conditions effective to obtain 2-(E)-hexen-1-al and either recovering the formed 2-(E)-hexen-1-al or reducing the 2-(E)-hexen-1-al to 2-(E)-hexen-1-ol and recovering the 2-(E)-hexen-1-ol from the medium.

12. A method of preparing a $C_6$- aldehyde, a $C_{12}$-oxocarboxylic acid, or their corresponding alcohols, from 13-hydroperoxy-octadeca-9,11-dienoic acid or 13 hydroperoxy-octadeca-9,11,15-trienoic acid, comprising (a) contacting the 13-hydroperoxy-octadeca-9,11-dienoic acid or the 13 hydroperoxy-octadeca-9,11,15-trienoic acid with a recombinant protein produced by a vector comprising a nucleic acid encoding a fatty acid 13-hydroperoxide lyase comprising the amino acid sequence set forth in SEQ ID NO:4, thereby converting the 13-hydroperoxy-octadeca-9,11-dienoic acid into the $C_6$-aldehyde and the $C_{12}$-oxocarboxylic acid; and either (b) recovering the $C_6$-aldehyde or the $C_{12}$-oxocarboxylic acid;

(b') reducing the $C_6$-aldehyde or the $C_{12}$-oxocarboxylic acid to their corresponding alcohols and recovering the alcohols; or (b") isomerizing the $C_6$-aldehyde or the $C_{12}$-oxocarboxylic acid under temperature and pH conditions effective to obtain the isomeric forms thereof and either recovering the isomeric forms or reducing the isomeric forms and recovering their corresponding alcohols from the medium.

13. A method of cleaving a 13-hydroperoxide of linoleic or α-linolenic acid into a $C_6$- aldehyde and a $C_{12}$-oxocarboxylic acid comprising contacting the 13-hydroperoxide with a recombinant protein produced by a vector comprising a nucleic acid encoding a fatty acid 13-hydroperoxide lyase comprising the amino acid sequence set forth in SEQ ID NO:6, thereby cleaving the 13-hydroperoxide.

14. A method of preparing n-hexanal, 3-(Z)-hexen-1-al, 2-(E)-hexen-1-al, or their corresponding alcohols from 13-hydroperoxy-octadeca-9,11-dienoic acid or 13 hydroperoxy-octadeca-9, 11, 15-trienoic acid, comprising (a) contacting the 13-hydroperoxy-octadeca-9,11-dienoic acid or the 13 hydroperoxy-octadeca-9,11,15-trienoic acid with a recombinant protein produced by a vector comprising a nucleic acid encoding a fatty acid 13-hydroperoxide lyase comprising the amino acid sequence set forth in SEQ ID NO:6, thereby converting the 13-hydroperoxy-octadeca-9, 11-dienoic acid into n-hexanal or the 13 hydroperoxy-octadeca-9,11,15-trienoic acid into 3-(Z)-hexen-1-al; and either (b) recovering the n-hexanal or 3-(Z)-hexen-1-al;

(b') reducing the n-hexanal into n-hexanol or the 3-(Z)-hexen-1-al into 3-(Z)-hexen-1-ol and recovering the hexanol or 3-(Z)-hexen-1-ol; or (b") isomerizing the 3-(Z)-hexen-1-al under temperature and pH conditions effective to obtain 2-(E)-hexen-1-al and either recovering the formed 2-(E)-hexen-1-al or reducing the 2-(E)-hexen-1-al to 2-(E)-hexen-1-ol and recovering the 2-(E)-hexen-1-ol from the medium.

15. A method of preparing a $C_6$- aldehyde, a $C_{12}$-oxocarboxylic acids or their corresponding alcohols, from 13-hydroperoxy-octadeca-9,11-dienoic acid or 13 hydroperoxy-octadeca-9, 11,15-trienoic avid, comprising (a) contacting the 13-hydroperoxy-octadeca-9,11-dienoic acid or the 13 hydroperoxy-octadeca-9, 11,15-trienoic acid with a recombinant protein produced by a vector comprising a nucleic acid encoding a fatty acid 13-hydroperoxide lyase comprising the amino acid sequence set forth in SEQ ID NO:6, thereby converting the 13-hydroperoxy-octadeca-9, 11-dienoic acid into the $C_6$-aldehyde and the $C_{12}$-oxocarboxylic acid; and either (b) recovering the $C_6$- aldehyde or the $C_{12}$-oxocarboxylic acid;

(b') reducing the $C_6$-aldehyde or the $C_{12}$-oxocarboxylic acid to their corresponding alcohols and recovering the alcohols; or (b") isomerizing the $C_6$- aldehyde or the $C_{12}$-oxocarboxylic acid under temperature and pH conditions effective to obtain the isomeric forms thereof and either recovering the isomeric forms or reducing the isomeric forms and recovering their corresponding alcohols from the medium.

* * * * *